US010875890B2

(12) United States Patent
Sikora et al.

(10) Patent No.: US 10,875,890 B2
(45) Date of Patent: Dec. 29, 2020

(54) **PEPTIDE INHIBITORS TARGETING THE *NEISSERIA GONORRHOEAE* PIVOTAL ANAEROBIC RESPIRATION FACTOR ANIA**

(71) Applicant: Oregon State University, Corvallis, OR (US)

(72) Inventors: Aleksandra Sikora, Corvallis, OR (US); Konstantin V. Korotkov, Lexington, KY (US)

(73) Assignees: Oregon State University, Corvallis, OR (US); The University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/489,707

(22) PCT Filed: Mar. 13, 2018

(86) PCT No.: PCT/US2018/022135
§ 371 (c)(1),
(2) Date: Aug. 29, 2019

(87) PCT Pub. No.: WO2018/169926
PCT Pub. Date: Sep. 20, 2018

(65) Prior Publication Data
US 2019/0389905 A1 Dec. 26, 2019

Related U.S. Application Data

(60) Provisional application No. 62/471,181, filed on Mar. 14, 2017.

(51) Int. Cl.
| A61K 38/08 | (2019.01) |
| A61K 38/10 | (2006.01) |
| A61K 38/00 | (2006.01) |
| A61K 45/06 | (2006.01) |
| C07K 7/06 | (2006.01) |
| C07K 7/08 | (2006.01) |
| A61P 31/04 | (2006.01) |

(52) U.S. Cl.
CPC ............... *C07K 7/06* (2013.01); *A61K 38/08* (2013.01); *A61K 45/06* (2013.01); *A61P 31/04* (2018.01)

(58) Field of Classification Search
CPC ........ A61K 38/08; A61K 38/10; A61K 38/00; A61K 45/06; C07K 7/06; C07K 7/08; A61P 31/04; G01N 2333/22; G01N 33/56911

USPC ........ 514/2.8, 21.5, 21.6; 530/300, 327, 328
See application file for complete search history.

(56) References Cited

U.S. PATENT DOCUMENTS

| 2004/0031072 A1* | 2/2004 | La Rosa | C07H 21/04 800/278 |
| 2004/0214272 A1* | 10/2004 | La Rosa | C07H 21/04 435/69.1 |
| 2007/0061916 A1* | 3/2007 | Kovalic | C07K 14/415 800/278 |
| 2007/0083334 A1* | 4/2007 | Mintz | G16B 40/00 702/19 |
| 2009/0312248 A1 | 12/2009 | Cocks et al. | |
| 2011/0262476 A1 | 10/2011 | Jennings | |
| 2013/0302855 A1* | 11/2013 | Selber | C07K 14/365 435/84 |
| 2014/0328862 A1* | 11/2014 | Scheid | C07K 16/1063 424/160.1 |

FOREIGN PATENT DOCUMENTS

WO    2015-065916    5/2015

OTHER PUBLICATIONS

Mills, RH. et al. "Abstract ID:12, Targeting Anaerobic Respiration for the Development of New Therapeutics Against Gonorrhea" In: 20th International Pathogenic Neisseria Conferenced, Sep. 4-9, 2016, Manchester, UK, Abstract.
Shewell, Luck K. et al., "Recombinant Truncated AniA of Pathogenic Neisseria Elicits a Non-Native Immune Response and Functional Blocking Antibodies", Biochemical and Biophysical Research Communications, 2013, vol. 431, pp. 215-220.
Sikora, Alexsandra et al., "Peptide Inhibitors Targeting the Neisseria Gonorrhoeae Pivotal Anaerobic Respiration Factor AniA", Antimicrobial Agents and Chemotherapy, Aug. 2017, vol. 61, Issue 8, Abstract, pp. 2-13.

* cited by examiner

*Primary Examiner* — Julie Ha
(74) *Attorney, Agent, or Firm* — Schwabe Williamson & Wyatt, P.C.

(57) ABSTRACT

Disclosed herein are peptide inhibitors of AniA. Pharmaceutical compositions are also disclosed that include one or more peptide inhibitors of AniA and/or nucleic acids encoding the same. The pharmacological inhibition of AniA should disable anaerobic respiration and augment the ability of existing antimicrobials to clear the pathogen. Thus, also disclosed are methods of inhibiting and/or treating infection from *N. gonorrhoeae*.

20 Claims, 10 Drawing Sheets
Specification includes a Sequence Listing.

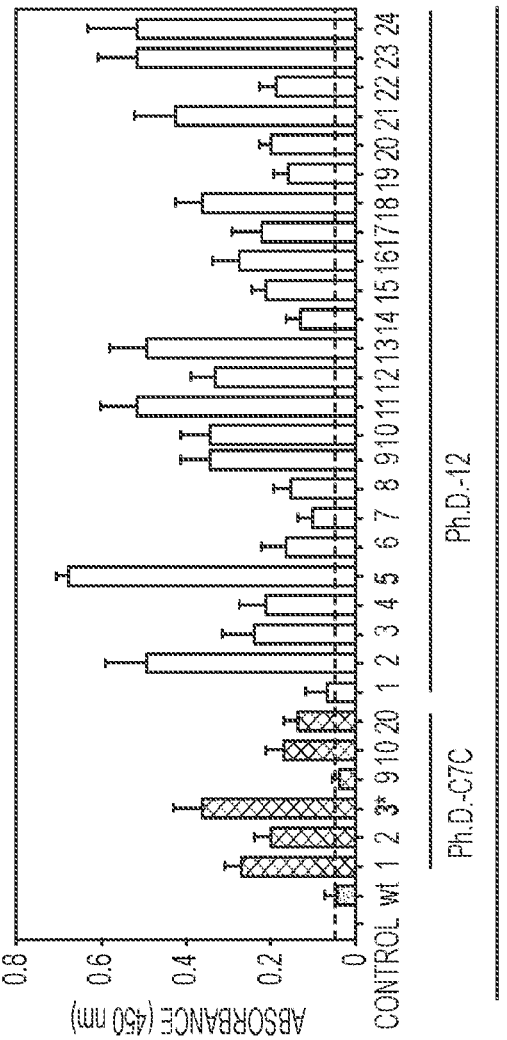
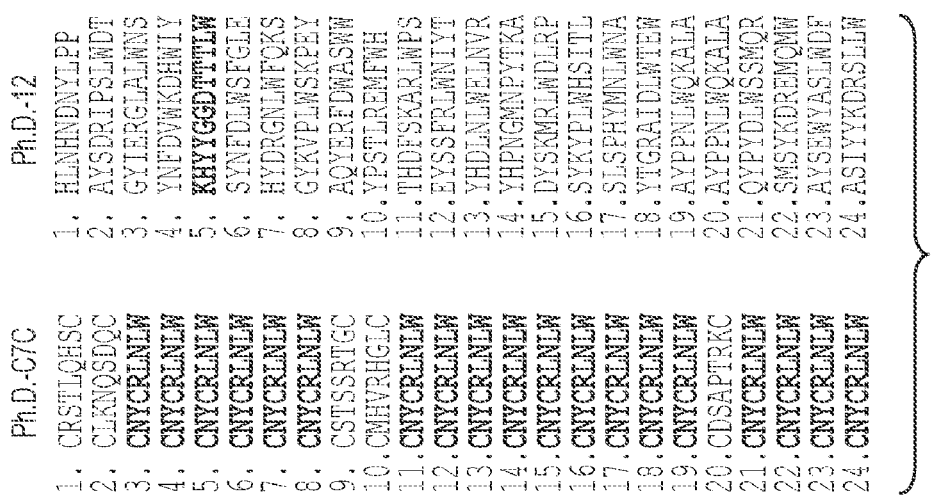
FIG. 3B
FIG. 3C

SEQUENCE LISTING

```
<160> NUMBER OF SEQ ID NOS: 66

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Lys His Tyr Tyr Gly Gly Asp Thr Thr Thr Leu Trp Gly Gly Gly Ser
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Ala Cys Asn Tyr Cys Arg Leu Asn Leu Trp Gly Gly Gly Ser
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide
```

-continued

```
<400> SEQUENCE: 3

Ala Cys Asn Tyr Ser Arg Leu Asn Leu Trp Gly Gly Gly Ser
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Ala Cys Ser Tyr Cys Arg Leu Asn Leu Trp Gly Gly Gly Ser
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide

<400> SEQUENCE: 5

Ala Cys Asn Phe Cys Arg Leu Asn Leu Trp Gly Gly Gly Ser
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide

<400> SEQUENCE: 6

Ala Cys Asn Ala Cys Arg Leu Asn Leu Trp Gly Gly Gly Ser
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Cys Asn Tyr Cys Arg Leu Asn Leu Trp
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Lys His Tyr Tyr Gly Gly Asp Thr Thr Thr Leu Trp
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9
```

Cys Asn Tyr Ser Arg Leu Asn Leu Trp
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Cys Ser Tyr Cys Arg Leu Asn Leu Trp
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Lys His Tyr Tyr Gly Asn Asp Thr Thr Thr Leu Trp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Lys His Tyr Tyr Gly Ser Asp Thr Thr Thr Leu Trp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Lys His Tyr Tyr Gly Gly Asp Thr Thr Ser Leu Trp
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

Lys His Tyr Tyr Gly Gly Glu Thr Thr Thr Leu Trp
1               5                   10

<210> SEQ ID NO 15
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 15
ctaccgccga aacgcctgca ggcgaactgc ccg                                       33

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 16
ccttaattaa gtctagagtc gccgggacgg ttggtcga                                  38

<210> SEQ ID NO 17
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 17
cagcctacac gcgtttcata atgttttcct tttgtaagaa aagtaggg                       48

<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 18
taattcccat agcgtttatt aaatcggata cccgtcatta gc                             42

<210> SEQ ID NO 19
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 19
gcctgcaggt ttaaacagtc ggcaaggcga ggcaacgc                                  38

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 20
tatgaaacgc gtgtaggctg gagctgct                                             28

<210> SEQ ID NO 21
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 21
aataaacgct atgggaatta gccatggtcc                                           30

<210> SEQ ID NO 22
<211> LENGTH: 18
<212> TYPE: DNA
<213> ORGANISM: Artificial Sequence

```
<220> FEATURE:
<223> OTHER INFORMATION: Synthetic oligonucleotide primer

<400> SEQUENCE: 22
gactgtttaa acctgcag                                                  18

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 23
gactctagac ttaattaagg atcc                                           24

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 24
ctgtcccatt ttgagagctc c                                              21

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 25
ccttgtgcgg cgcaatag                                                  18

<210> SEQ ID NO 26
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 26
ctgttaatta aaaaaggaaa acattatcaa acgcc                               35

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 27
gctaatgacg ggtatccgat                                                20

<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 28
cgcacaacgt cgccttccac gccgcaa                                        27
```

<210> SEQ ID NO 29
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 29
ttgcggcgtg gaaggcgacg ttgtgcg                                27

<210> SEQ ID NO 30
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 30
gaacttggtg tcttccttcg ccgtcatcgg cgaaatcttc                  40

<210> SEQ ID NO 31
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 31
gaagatttcg ccgatgacgg cgaaggaaga caccaagttc                  40

<210> SEQ ID NO 32
<211> LENGTH: 47
<212> TYPE: DNA
<213> ORGANISM: Artificial Sequence
<220> FEATURE:
<223> OTHER INFORMATION: Synthetic oligonucleotide primer

<400> SEQUENCE: 32
gaaccgccgg caggcacgat ggtgctttgt acgttttcgt taatcag          47

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 33
cgtgcctgcc ggcggttc                                          18

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 34
gcgtttcggc ggtagcttgt g                                      21

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 35
ccctcatagt tagcgtaacg                                              20

<210> SEQ ID NO 36
<211> LENGTH: 1179
<212> TYPE: DNA
<213> ORGANISM: Neisseria gonorrhoeae

<400> SEQUENCE: 36
atgaaacgcc aagcattagc cgcaatgatt gcttccttat tcgcattggc cgcctgcggc     60
ggcgaacctg ccgcgcaagc ccctgccgaa acccctgccg cttccgcaga agccgcaagt    120
tccgccgcac aagctaccgc cgaaacgcct gcaggcgaac tgcccgtcat cgatgcggtg    180
accacccacg ctcccgaagt acctcccgca atcgaccgcg actatcctgc caaagtacgc    240
gtaaaaatgg aaaccgtcga aaaaaccatg aaaatggacg acggggtgga ataccgctac    300
tggacatttg acgcgacgt tccgggccgt atgatccgcg tacgcgaagg cgataccggtt    360 gaagtcgaat tctccaacaa tccttcttct accgttccgc acaacgtcga cttccacgcc    420
gcaaccggtc agggcggcgg tgcagccgcg acctttaccg ccccgggccg cacttccaca    480
ttcagcttca aagccctgca accgggcctg tacatctacc actgcgccgt cgcgccggtc    540
ggtatgcaca tcgccaacgg tatgtacggt ctgattttgg tcgagcctaa gaaggcctg    600 ccgaaagtgg ataaagagtt ctacatcgtc caaggcgact tctacaccaa aggcaaaaaa    660
ggcgcgcaag gcctgcaacc gttcgatatg gacaaagccg ttgccgaaca gcctgaatac    720
gtcgtattca acggccacgt aggcgctatc gccggcgata cgccctgaa agccaaagca    780 ggcgaaaccg tgcgtatgta cgtcggtaac ggcggcccga acttggtgtc ttccttccac    840
gtcatcggcg aaatcttcga caaagtttat gttgaaggcg gcaaactgat taacgaaaac    900
gtacaaagca ccatcgtgcc tgccggcggt tctgccatcg tcgaattcaa agtcgacatc    960
ccgggcaact acactttggt cgaccactcc atcttccgcg cattcaacaa aggcgcgttg   1020
gggcaattga agtagaggg tgcggaaaac cctgaaatca tgactcaaaa attgagtgat   1080
accgcttacg ccggcagcgg cgcggcttct gcccctgctg cttccgcacc ggctgcttct   1140
gccccggcag cctctgcatc cgaaaaaagc gtttattaa                          1179

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa can be Asn or Ser
<220> FEATURE:
<221> NAME/KEY: MISC_FEATURE
<222> LOCATION: (4)..(4)
<223> OTHER INFORMATION: Xaa can be Asn or Ser

<400> SEQUENCE: 37

Cys Xaa Tyr Xaa Arg Leu Asn Leu Trp
1               5

<210> SEQ ID NO 38
<211> LENGTH: 4
<212> TYPE: PRT
<213> ORGANISM: Artificial Sequence

```
<220> FEATURE:
<223> OTHER INFORMATION: Synthetic peptide

<400> SEQUENCE: 38

Gly Gly Gly Ser
1

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Cys Arg Ser Thr Leu Gln His Ser Cys
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Cys Leu Lys Asn Gln Ser Asp Gln Cys
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Cys Ser Thr Ser Ser Arg Thr Gly Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Cys Met His Val Arg His Gly Leu Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Cys Asp Ser Ala Pro Thr Arg Lys Cys
1               5

<210> SEQ ID NO 44
<211> LENGTH: 11
<212> TYPE: PRT
<213> ORGANISM: Artificial Sequence
<220> FEATURE:
```

```
<223> OTHER INFORMATION: Synthetic peptide

<400> SEQUENCE: 44

His Leu Asn His Asn Asp Asn Tyr Leu Pro Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic peptide

<400> SEQUENCE: 45

Ala Tyr Ser Asp Arg Ile Pro Ser Leu Trp Asp Thr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide

<400> SEQUENCE: 46

Gly Tyr Ile Glu Arg Gly Leu Ala Leu Trp Asn Ser
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic peptide

<400> SEQUENCE: 47

Tyr Asn Phe Asp Val Trp Lys Asp His Trp Ile Tyr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic peptide

<400> SEQUENCE: 48

Ser Tyr Asn Phe Asp Leu Trp Ser Phe Gly Leu Glu
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic peptide

<400> SEQUENCE: 49

His Tyr Asp Arg Asp Asn Leu Trp Phe Gln Lys Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 50

Gly Tyr Lys Val Pro Leu Trp Ser Lys Pro Glu Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide

<400> SEQUENCE: 51

Ala Gln Tyr Glu Arg Phe Asp Trp Ala Ser Trp Trp
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide

<400> SEQUENCE: 52

Tyr Pro Ser Thr Leu Arg Glu Met Phe Trp His
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic peptide

<400> SEQUENCE: 53

Thr His Asp Phe Ser Lys Ala Arg Leu Trp Pro Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

Glu Tyr Ser Ser Phe Arg Leu Trp Asn Ile Tyr Thr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide

<400> SEQUENCE: 55

Tyr His Asp Leu Asn Leu Trp Glu Leu Asn Val Arg
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 56

Tyr His Pro Asn Gly Met Asn Pro Tyr Thr Lys Ala
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide

<400> SEQUENCE: 57

Asp Tyr Ser Lys Met Arg Leu Trp Asp Leu Arg Pro
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic peptide

<400> SEQUENCE: 58

Ser Tyr Lys Tyr Pro Leu Trp His Ser Ile Thr Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic peptide

<400> SEQUENCE: 59

Ser Leu Ser Pro His Tyr Met Asn Leu Trp Asn Ala
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic peptide

<400> SEQUENCE: 60

Tyr Thr Gly Arg Ala Ile Asp Leu Trp Thr Glu Trp
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic peptide

<400> SEQUENCE: 61

Ala Tyr Pro Pro Asn Leu Trp Gln Lys Ala Leu Ala
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic peptide

<400> SEQUENCE: 62
```

```
Ala Tyr Pro Pro Asn Leu Trp Gln Lys Ala Leu Ala
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic peptide

<400> SEQUENCE: 63

Gln Tyr Pro Tyr Asp Leu Trp Ser Ser Met Gln Arg
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic peptide

<400> SEQUENCE: 64

Ser Met Ser Tyr Lys Asp Arg Glu Met Gln Met Trp
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic peptide

<400> SEQUENCE: 65

Ala Tyr Ser Glu Trp Tyr Ala Ser Leu Trp Asp Phe
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic peptide

<400> SEQUENCE: 66

Ala Ser Ile Tyr Tyr Lys Asp Arg Ser Leu Leu Trp
1               5                   10
```

PEPTIDE INHIBITORS TARGETING THE *NEISSERIA GONORRHOEAE* PIVOTAL ANAEROBIC RESPIRATION FACTOR ANIA

CROSS REFERENCE TO RELATED APPLICATION

This application is a national phase entry under 35 U.S.C. § 371 of International Application No. PCT/US2018/022135 filed Mar. 13, 2018, entitled "PEPTIDE INHIBITORS TARGETING THE *NEISSERIA GONORRHOEAE* PIVOTAL ANAEROBIC RESPIRATION FACTOR AniA," which designated among the various State, the United States of America, and which claims the priority benefit of the earlier filing date of U.S. Provisional Application No. 62/471,181, filed Mar. 14, 2017, which is hereby specifically incorporated herein by reference in its entirety.

STATEMENT OF GOVERNMENT SUPPORT

This invention was made with government support under grant number R01-AI117235 awarded by National Institute of Allergy and Infectious Diseases, National Institutes of Health and grant numbers P20GM103486 and P30GM110787awarded by National Institute of General Medical Sciences of the National Institutes of Health. The government has certain rights in the invention.

TECHNICAL FIELD

This disclosure relates to peptides that target the *Neisseria gonorrhoeae* anaerobic respiration factor AniA and methods of treating or inhibiting *Neisseria gonorrhoeae* infection using the same.

BACKGROUND

Among human-colonizing *Neisseria* species only *Neisseria gonorrhoeae*, the causative agent of gonorrhea, is considered pathogenic. Gonorrhea remains a serious public health concern with 78 million new cases annually worldwide, severe consequences on reproductive and neonatal health, and contribution to transmission and acquisition of HIV (Newman et al. 2015, PLoS One 10:e0143304; Fleming and Wasserheit 1999, Sex Transm Infect 75:3-17). Untreated or inadequately treated infections can result in endometritis, pelvic inflammatory disease, ectopic pregnancy, epididymitis and infertility (Edwards and Apicella 2004, Clin Microbiol Rev 17:965-81, table of contents; Woods 2005, Semin Pediatr Infect Dis 16:258-70; Campbell 1928, Ann Surg 88:98-111). During pregnancy, gonorrhea may lead to chorioamnionitis, which is additionally complicated by septic abortion, premature rupture of membranes, and preterm delivery (Westrom 1994, Sex Transm Dis 21:S32-7). Infants born to infected mothers have increased risk of ophthalmia neonatorum, which can lead to blindness. There is a pressing need for development of new antibiotics, antibiotic surveillance strategies, and *gonorrhoeae* vaccine as *N. gonorrhoeae* strains resistant to the last effective treatment options are emerging and clinical treatment failures have been documented (Ohnishi et al. 2011, Antimicrob Agents Chemother 55:3538-45; Yokoi et al. 2007, Emerg Infect Dis 13:1275-7; Unemo et al. 201, Sex Transm Infect 86:442-4; Ison 2011, Euro Surveill 16; Allen et al. 2013, JAMA 309:163-70; Tapsall et al. 2009, J Med Microbiol 58:683-7; Unemo and Nicholas 2012, Future Microbiol 7:1401-22; Ison et al. 2013, Sex Transm Infect 89 Suppl 4:iv52-6; Unemo and Shafer 2014; Clin Microbiol Rev 27:587-613). *N. gonorrhoeae*, initially considered as an obligate aerobic bacterium, survives and proliferates in a milieu of obligate anaerobes within the genitourinary tract (Smith 1975. The pathogenic anaerobic bacteria, 2nd ed. ed. Charles C. Thomas Publisher, Springfield, Ill.). Pioneering work by Short et. al. (Short et al. 1982.; J Clin Microbiol 15:915-9) demonstrated that various gonococci including laboratory strains and fresh clinical isolates remained viable during anaerobic inoculation. Subsequently, nitrite was identified as the critical terminal electron acceptor supporting *N. gonorrhoeae* growth under oxygen-limited conditions (Knapp and Clark 1984; Infect Immun 46:176-81). Mounting evidence demonstrates that anaerobic life style is an important state during infection and about 10% of the *N. gonorrhoeae* genome comprises the anaerobic stimulon (Whitehead et al. 2007, BMC Genomics 8:35; Isabella and Clark 2011, BMC Genomics 12:51; Falsetta et al. 2009, Infect Immun 77:3522-32; Phillips et al. 2012, PLoS One 7:e38303). *N. gonorrhoeae* favors anaerobic respiration during growth in biofilms (Falsetta et al. 2009, 77:3522-32.; Phillips et al. 2012, PLoS One 7:e38303; Steichen et al. 2011, Infect Immun 79:1504-11). Bacteria in biofilms display increased resistance to antimicrobials and host defense mechanisms and the naturally occurring *N. gonorrhoeae* biofilms are linked with persistent infections in women (Steichen et al. 2011, Infect Immun 79:1504-11; Costerton et al. 1999, Science 284:1318-22; Fux et al. 2005, Trends Microbiol 13:34-40; Hoiby et al. 2010, Int J Antimicrob Agents 35:322-32).

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 1A shows a schematic illustration of AniA function in the *Neisseria gonorrhoeae* denitrification pathway. A two-step denitrification pathway in *N. gonorrhoeae* is comprised of AniA (NGO1276), that reduces nitrite to nitric oxide, and NorB, which subsequently reduces nitric oxide to nitrous oxide. FIGS. 1B and 1C shows the crystal structure of AniA trimer shown in ribbon representation with three subunits (B and C show a side and a top view, respectively). Each monomer contains two $Cu^{2+}$ ions shown as spheres. FIG. 1D shows a diagram of native AniA and recombinant variant proteins, sAniA and mutated AniA D137A H280A. A signal peptide (SP) amino acids 1-20; N-terminal cupredoxin domain, aa 102-198; C-terminal cupredoxin domain, aa 205-348; the C-terminal 6 His tag; the active site residues: aspartate (D137) and histidine (H280) are shown. FIG. 1E illustrates the effect of genetic inactivation of aniA and point mutations, D137A H280A, on *N. gonorrhoeae* survival under anoxia. The wild type FA1090 (wt), the isogenic knockout ΔaniA, the complemented strain ΔaniA/$P_{lac}$aniA, and ΔaniA strain carrying mutated version of AniA, ΔaniA/$P_{lac}$aniA D137A H280A, were grown in broth to an $OD_{600}$ of 0.2, were serially diluted and spotted onto solid media supplemented with nitrite and 0.1 mM IPTG. Growth was examined after 22 and 48 h incubation in aerobic and anaerobic conditions, respectively. FIG. 1F shows measurements of the nitrite reductase activity of AniA using a fluorometric [2,3-diaminophtalene (DAN assay). The consumption of nitrite was examined at 37° C. under anaerobic conditions in a solution containing sodium nitrite, methyl viologen, sodium dithionate, Tris-HCL pH 7.0, and either decreasing concentrations of sAniA (as indicated) or D137A H280A (1 µM). The data show means of reaction rate with associated SEMs (n=10).

FIGS. 3A-3C illustrate targeting AniA using a phage display approach. FIG. 3A shows that the recombinant version of AniA, sAniA, was purified to homogeneity and used in affinity capture method as bait during three panning experiments with two phage display libraries expressing either randomized linear 12-mer peptides (Ph.D.-12) or randomized 7-mer peptides flanked by a pair of cysteine residues (Ph.D.-C7C). As a first step in every round of the panning experiment both peptide libraries were pre-cleared against Ni-NTA magnetic chitin resin to remove non-specifically binding peptides. The supernatants from this step were then added to 200 µg of sAniA bound to the resin. After incubation with the protein, unbound phages were washed away using TBST with increasing stringency of the washing in consecutive rounds. The elutions were performed with glycine-HCL (pH 2.2). FIG. 3B shows the deduced peptide sequences of the 7-mer and 12-mer peptides obtained by sequencing of the DNA of 24 randomly selected phages from each group eluted after the third round of biopanning (SEQ ID NOS: 7, 8, and 39-66). These studies revealed 26 unique peptides, with one of them, C7-3, identified multiple times. Synthesized peptides are shown in bold. FIG. 3C illustrates the evaluation of identified peptides through phage ELISA. Phage clones were purified and tested separately to measure their affinity to sAniA in the phage ELISA assay. The purified sAniA (2 µM) was coated overnight at 4° C. to 96-well flat bottom plates. After the coating step, unbound sAniA was removed and the wells were thoroughly washed with the storage buffer. The wells were blocked, and incubated with $10^{10}$ PFU per well from each amplification. After washing, the anti-M13 monoclonal antisera coupled to horseradish peroxidase were added. Unbound antisera were removed by excessive washing and enzymatic activity was exerted by the addition of Turbo TMB ELISA. Absorbance at 450 nm was measured. Readings were compared to wells, which underwent identical treatment but lacked sAniA (control) and to signal from a wild type phage, M13KE (of $10^{10}$ PFU), that does not display peptides (wild type). The mean and SEMs from seven independent experiments are shown. *Identified multiple times.

FIGS. 6A-B show the binding mode of C7-3 (A) and 12-5 (B) in the $Cu^{2+}$ active site of AniA homotrimer. Peptides C7-3 (A) and 12-5 (B) bound in the AniA pocket with distinct conformation. These conformations depended essentially on the residues sequence composing the peptide. Afterward, the initial conformation of the peptide (stable conformation in the solvent) was slightly perturbed during the docking procedure due to the interactions with the receptor. FIG. 6C shows the inhibition of nitrite reductase activity of sAniA. Nitrite reductase inhibition plot of sAniA with synthetic peptides C7-3, 12-5 and mutated variants of C7-3 (C7-3m1, C7-3m2, C7-3P, and C7-3A). sAniA was pre-incubated with various concentrations (0-100 µM) of synthetic peptides for 1 h at room temperature following measurement of nitrite reductase activity with DAN. Percent inhibition was calculated using the formula % I=100*(1−(x−y)/(z−y)) where "x", "y" and "z" are the concentrations of nitrite in samples containing sAniA incubated with synthetic peptides, AniA D137AH280A and sAniA, respectively. FIG. 6D shows the inhibition of nitrite reductase activity of intact *N. gonorrhoeae* cells. Nitrite reductase inhibition of AniA was assessed using intact gonococci. Bacteria were pre-incubated with different concentrations of synthetic peptides (0, 0.6, 0.3, and 0.15 mM) for 1 h followed by measurement of nitrite reductase activity using DAN. Percent inhibition was calculated using the formula % I=100*(1−(x−y)/(z−y)) where "x", "y" and "z" are the concentrations of nitrite in samples containing FA1090 $\Delta$aniA/$P_{lac}$aniA incubated with synthetic peptides, $\Delta$aniA/$P_{lac}$aniAD137AH280A and $\Delta$aniA/$P_{lac}$aniA, respectively. FIG. 6E shows the kinetic analyses of the interaction between AniA and C7-3. Binding affinity between AniA and C7-3 peptide were measured using biolayer interferometry. Biotinylated C7-3 peptide was immobilized on streptavidin coated sensor and incubated with increasing concentration of recombinant AniA (50-1000 nM). Experiments were repeated on three separate occasion and the dissociation constants were calculated by globally fitting the curves with 2:1 binding kinetics. The determined $K_D$ for C7-3 was [775±88.5 nM (average±SEM of three independent experiments)].

FIGS. 8A and 8B shows the analysis of single nucleotide polymorphisms in aniA. Analysis of aniA (locus NGO1276) in 42,088 *Neisseria* spp genomes deposited into PubMLST database (available on the world wide web at pubmlst.org/neisseria/ as of Jan. 25, 2017 (SEQ ID NO: 36)) showed that there are 318 aniA alleles and 395 single nucleotide polymorphic sites.

DETAILED DESCRIPTION OF DISCLOSED EMBODIMENTS

Figure 1A:
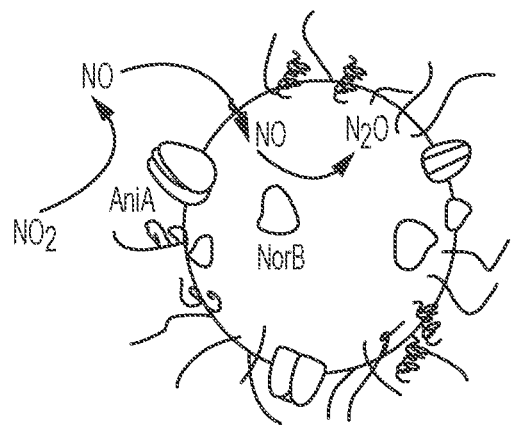
FIGS. 1A-1F illustrate a structural and functional analysis of AniA.
Figure 1B:
Figure 1C:
Figure 1D:
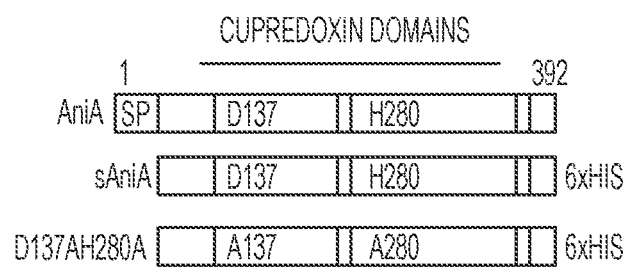
Figure 1E:
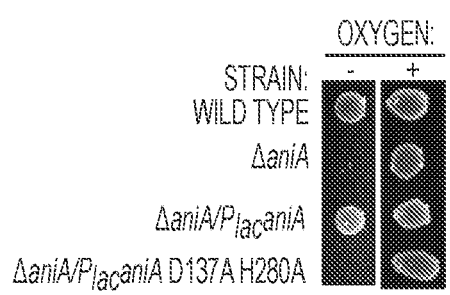
Figure 1F:
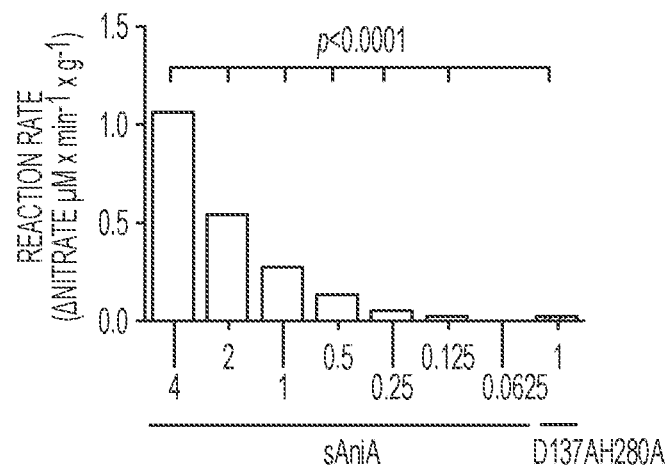

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999. In addition, the materials, methods, and examples are illustrative only and not intended to be limiting.

A. Introduction

*Neisseria gonorrhoeae* causes the sexually transmitted infection, gonorrhea, which is highly prevalent worldwide and has a major impact on reproductive and neonatal health. The "superbug" status of *N. gonorrhoeae* necessitates development of drugs with different mechanism of action. Here, the inventors have focused therapeutic efforts on targeting the nitrite reductase AniA, which is a pivotal component of the *N. gonorrhoeae* anaerobic respiration and biofilm formation.

In *N. gonorrhoeae* anaerobic growth is accomplished by the utilization of a two-step denitrification pathway including AniA (NGO1276), a copper-containing enzyme that reduces nitrite to nitric oxide, which is subsequently reduced to nitrous oxide by NorB (NGO1275; see FIG. 1). The denitrification pathway is truncated as it lacks nitrous oxide reductase complex (Boulanger and Murphy 2002, J Mol Biol 315:1111-27; Mellies et al. 1997, Mol Gen Genet 256:525-32; Householder et al. 2000, Infect Immun 68:5241-6; Barth et al. 2009, Microbiology 155:4093-103). AniA (formerly Pan 1), also known as NirK, is a surface-exposed glycosylated lipoprotein prerequisite for *N. gonorrhoeae* viability under oxygen-limited conditions and enhancing gonococci survival upon exposure to normal human serum (Falsetta et al. 2009, Infect Immun 77:3522-32; Phillips et al. 2012, PLoS One 7:e38303; Shewell et al. 2013, Biochem Biophys Res Commun 431:215-20). Nitrite reductase, in addition to Ccp, cytochrome c', and Laz, provides pathogenic *Neisseria* with a protection against assaults from reactive oxygen and nitrogen species (Turner et al. 2003, Biochem J 373:865-73.; Turner et al. 2005, Biochem J 388:545-53). Further, antibodies to AniA have been found in sera from infected women, demonstrating that aniA is expressed in vivo (Knapp and Clark 1984, Infect Immun 46:176-81; Clark et al. 1988, Microb Pathog 5:381-90). For these reasons, AniA's has demonstrated potential as a gonorrhea vaccine candidate (Shewell et al. 2013, Biochem Biophys Res Commun 431:215-20; Jerse et al. 2014, Vaccine 32:1579-87).

The inventors' studies have shown that gonococci expressing AniA containing altered catalytic residues, D137A and H280A, failed to grow under anaerobic conditions demonstrating that the nitrite reductase function warrants bacterial viability. As disclosed herein, the inventors have identified AniA as a target for pharmacological intervention against gonorrhea. While not being bound by theory, it is believed that the pharmacologic inhibition of AniA reduces fitness of gonococcus in the genital tract, where oxygen tension is reduced, and augments the ability of existing antimicrobials to clear the pathogen from a subject. To facilitate the pharmacological targeting of AniA, new crystal structures of AniA were refined to 1.90 Å and 2.35 Å resolution and a phage-display approach with libraries expressing randomized linear dodecameric peptides or heptameric peptides flanked by a pair of cysteine residues was utilized. These trials enabled the identification of 29 unique peptides, with one of them, C7-3, identified multiple times. Evaluation of their ability to interact with AniA using enzyme-linked immunosorbent assay and computational docking established C7-3 as an inhibitor binding near the type II copper site of the enzyme. Subsequent enzymatic assays with a purified AniA as well as whole-cell nitrite utilization studies, and bio-layer interferometry with a synthetic C7-3 and its derivatives confirmed the strong inhibitory effect on the AniA nitrite reductase activity.

B. Description of Several Embodiments

Disclosed herein are peptide inhibitors of AniA and nucleic acids encoding such peptides. Pharmaceutical compositions are also disclosed that include one or more peptide inhibitors of AniA and/or nucleic acids encoding the same. The pharmacological inhibition of AniA should disable anaerobic respiration and augment the ability of existing antimicrobials to clear the pathogen. Thus, also disclosed are methods of inhibiting and/or treating infection from *N. gonorrhoeae*, and/or inhibition of the enzymatic activity of AniA.

In embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as $CX_1YX_2RLNLW$ (SEQ ID NO: 37), wherein $X_1$ can be a N or S, wherein $X_2$ can be a N or S. In certain embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as CNYCRLNLW (SEQ ID NO: 7). In certain embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as CNYSRLNLW (SEQ ID NO: 9). In certain embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as CSYCRLNLW (SEQ ID NO: 10). In certain embodiments, a peptide inhibitor of AniA comprises an N-terminal leader sequence, such as a single amino acid for example an alanine. In other examples the leader sequence includes multiple amino acid residues, for example to aid in translation/transcription and/or cellular/subcellular localization. In certain embodiments, a peptide inhibitor of AniA comprises a C-terminal sequence, such as the amino acid sequence set forth as GGGS (SEQ ID NO: 38). In certain embodiments, additional amino acids are added to the C or N terminus to aid in stabilization and/or solubility of the peptide. In certain embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as ACNYCRLNLWGGGS (SEQ ID NO: 2), In certain embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as ACNYSRLNLWGGGS (SEQ ID NO: 3), In certain embodiments, a peptide inhibitor of AniA comprises, consists essentially of, and/or consists of, an amino acid sequence that is at least 95% identical, such as at least 96%, at least 97%, at least 98%, at least 99%, or even 100% identical to the amino acid sequence set forth as ACSYCRLNLWGGGS (SEQ ID NO: 4), In certain embodiments a peptide inhibitor of AniA, includes a detectable marker, such as biotin, or other marker, for example linked to a C-terminal, N-terminal, and/or internal residue of the peptide.

In some embodiments, a disclosed composition, such as a therapeutic and/or pharmacological composition includes one or more of peptides having the amino acid sequence that is at least 95% identical such as at least 96%, at least 97%, at least 98%, at least 99%, or even 100% identical to one of the amino acid sequences set forth as set forth as SEQ ID NO: 37, SEQ ID NO: 7, SEQ ID NO: 9, SEQ ID NO: 10, SEQ ID NO: 2, SEQ ID NO: 3, and SEQ ID NO: 4, such as 2 or more, 3 or more, 4 or more, 5 or more, or 6 or more, in any combination.

The disclosed isolated peptides include synthetic embodiments of peptides described herein. In addition, analogs (non-peptide organic molecules), derivatives (chemically functionalized peptide molecules obtained starting with the disclosed peptide sequences) and variants (homologs) of these peptides can be utilized in the methods described herein. Each peptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. In another example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a peptide having measurable or enhanced ability to inhibit AniA. For computer modeling applications, a pharmacophore is an idealized three-dimensional definition of the structural requirements for biological activity. Peptido- and organomimetics can be designed to fit each pharmacophore with current computer modeling software.

In embodiments, a peptide inhibitor of AniA is included in a fusion protein. For example, any and all of the peptide inhibitors of AniA included in a composition, including a plurality of peptide inhibitors of AniA, can be in the form of a fusion protein. Thus, the fusion protein can include a peptide inhibitor of AniA and a second heterologous moiety, such as a myc protein, an enzyme or a carrier (such as a hepatitis carrier protein or bovine serum albumin) covalently linked to the peptide inhibitor of AniA. A second heterologous moiety can be covalently or non-covalently linked to the peptide inhibitor of AniA. The peptide inhibitor of AniA can be included in a fusion protein and can also include heterologous sequences. Thus, in several specific non-limiting examples, one or more of the peptide inhibitors of AniA are included in a fusion peptide, for example a fusion of a peptide inhibitor of AniA with six sequential histidine residues, a β-galactosidase amino acid sequence, or other amino acid sequence. The peptide inhibitor of AniA can also be covalently linked to a carrier. The compositions described herein can include varying concentrations of one or more peptide inhibitors of AniA in a plurality of peptide inhibitors of AniA.

Nucleic acids encoding one or more of peptide inhibitors of AniA are envisioned. These polynucleotides include DNA, cDNA and RNA sequences which encode the peptide(s) of interest. Nucleic acid molecules encoding these peptides can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same peptide.

Nucleic acid sequences encoding one or more of the peptide inhibitors of AniA can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68: 109-151, 1979; the diethylphosphoramidite method of Beaucage et al., Tetra. Lett. 22: 1859-1862, 1981; the solid phase phosphoramidite triester method described by Beaucage & Caruthers, Tetra. Letts. 22(20): 1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding one or more of the peptide inhibitors of AniA disclosed herein can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Once the nucleic acids encoding one or more of the peptide inhibitors of AniA are isolated and cloned, the peptide can be expressed in a recombinantly engineered cell such as bacteria, plant, yeast, insect and mammalian cells using a suitable expression vector. One or more DNA sequences encoding one or more immunogenic peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding one or more of peptide inhibitors of AniA can be operatively linked to expression control sequences (e.g., a promoter). An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding one or more of peptide inhibitors of AniA can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

The peptide inhibitors of AniA can be administered in vitro, ex vivo or in vivo to a cell or subject. It is desirable to prepare peptide inhibitors of AniA as a pharmaceutical composition appropriate for the intended application, for example to inhibit or treat an infection from N. gonorrhoeae. Accordingly, methods for making a medicament or pharmaceutical composition containing a peptide inhibitor of AniA are included herein. Peptide inhibitors of AniA can be prepared for administration alone or with other active ingredients, such as antibiotics (for example the antibiotics described herein) and/or other proteins. In some examples, a therapeutic composition includes a peptide inhibitor of AniA. In some examples, a therapeutic composition includes an antibiotic. In some examples, a therapeutic composition includes a peptide inhibitor of AniA and an antibiotic. When a peptide inhibitor of AniA and antibiotic is administered to a subject, the administration can be concurrent or sequential. Sequential administration of the can be separated by any amount of time. Multiple administrations of the compositions described herein are also contemplated.

In some embodiments, a disclosed therapeutic composition includes a therapeutically effective amount of isolated peptide inhibitor of AniA includes an amino acid sequence that is at least 95% identical such as at least 96%, at least 97%, at least 98%, at least 99%, or even 100% identical to set forth as SEQ ID NO: 37, SEQ ID NO: 7, SEQ ID NO: 9, SEQ ID NO: 10, SEQ ID NO: 2, SEQ ID NO: 3, and SEQ ID NO: 4, and/or a nucleic acid encoding such a peptide, and optionally a therapeutically effective amount of an antibiotic, or even more than one antibiotic.

Typically, preparation of a pharmaceutical composition (for use as a medicament or in the manufacture of a medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow the peptide inhibitor of AniA to interact with cells in a subject, such as *N. gonorrhoeae* cells. Administration of therapeutic compositions can be by any common route. This includes oral, nasal (such as intranasal), ocular, buccal, enteral, intravitral, or other mucosal (such as rectal or vaginal) or topical administration. Alternatively, administration will be by orthotopic, intradermal subcutaneous, intramuscular, parentral intraperitoneal, or intravenous injection routes. Such pharmaceutical compositions are usually administered as pharmaceutically acceptable compositions that include physiologically acceptable carriers, buffers or other excipients.

Pharmaceutical compositions can include an effective amount (such as a therapeutically effective amount) of a peptide inhibitor of AniA and optionally an antibiotic (for example, dissolved or suspended) in a pharmaceutically acceptable carrier or excipient. Pharmaceutically acceptable carriers and/or pharmaceutically acceptable excipients are known in the art and are described, for example, in Remington's Pharmaceutical Sciences, by E. W. Martin, Mack Publishing Co., Easton, Pa., 15th Edition (1975).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include a peptide inhibitor of AniA in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms. Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders.

In some examples, a subject is selected that has or is at risk of a *N. gonorrhoeae* infection. The methods include administering to the subject a therapeutically effective amount of an isolated peptide inhibitor of AniA that includes an amino acid sequence that is at least 95% identical such as at least 96%, at least 97%, at least 98%, at least 99%, or even 100% identical to set forth as SEQ ID NO: 37, SEQ ID NO: 7, SEQ ID NO: 9, SEQ ID NO: 10, SEQ ID NO: 2, SEQ ID NO: 3, and SEQ ID NO: 4, and/or a nucleic acid encoding such a peptide, and optionally a therapeutically effective amount of an antibiotic, or even more than one antibiotic. Various modes of administration of the pharmaceutical compositions of this disclosure are contemplated (see below).

As disclosed herein the administration of the peptide inhibitor of AniA in conjunction with an antibiotic increases the effectiveness of the antibiotic, for example allowing a lower dose to be used and/or increasing bacterial clearance Typical subjects intended for treatment with the pharmaceutical compositions and methods of the present disclosure include humans, as well as non-human primates and other animals. To identify subjects for prophylaxis or treatment according to the methods of the disclosure, accepted screening methods are employed to determine risk factors associated with a targeted or suspected disease or condition (for example, an infection associated with *N. gonorrhoeae*) or to determine the status of an existing disease or condition in a subject. These screening methods include, for example, diagnostic methods, such as various ELISA and other immunoassay methods, which are available and well known in the art to detect and/or characterize disease-associated markers. These and other routine methods allow the clinician to select patients in need of therapy using the methods and compositions of the disclosure.

An effective amount of the pharmaceutical composition is determined based on the intended goal, for example to inhibit and/or treat a *N. gonorrhoeae* infection of a human or non-human subject. The administration of the pharmaceutical compositions of the disclosure can be for either prophylactic or therapeutic purpose. When provided prophylactically, the pharmaceutical composition is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of a peptide inhibitor of AniA (for example, amounts that are effective to alleviate one or more symptoms of $N.$ $gonorrhoeae$ infection).

The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes both a peptide inhibitor of AniA alone or in conjunction with an antibiotic, time and route of administration, other drugs or treatments being administered concurrently, as well as the specific pharmacology of the therapeutic compositions for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a peptide inhibitor of AniA and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight. When administered to a subject, a dosage will generally be used that will achieve target tissue concentrations that has been shown to achieve an in vitro or in vivo effect.

In general any antibiotic can be used with the disclosed composition or methods. Examples of antibiotics that can be used include but are not limited to aminoglycosides (such as amikacin, gentamicin, kanamycin, neomycin, netilmicin, streptomycin, tobramycin, and paromomycin); ansamycins (such as geldanamycin, and herbimycin); carbacephems (such as loracarbef, ertapenem, doripenem, imipenem/cilastatin, and meropenem); cephalosporins (such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and ceftobiprole); glycopeptides (such as teicoplanin and vancomycin); macrolides (such as azithromycin, clarithromycin, dirithromycin, erythromycin, roxithromycin, troleandomycin, telithromycin, and spectinomycin); monobactams (such as aztreonam); penicillins (such as amoxicillin, ampicillin, azlocillin, carbenicillin, cloxacillin, dicloxacillin, flucloxacillin, mezlocillin, meticillin, nafcillin, oxacillin, penicillin, piperacillin, and ticarcillin); peptides (such as bacitracin, colistin, and polymyxin b); quinolones (such as ciprofloxacin, enoxacin, gatifloxacin, levofloxacin, lomefloxacin, moxifloxacin, norfloxacin, ofloxacin, trovafloxacin, grepafloxacin, and sparfloxacin); sulfonamides (such as mafenide, prontosil (archaic), sulfacetamide, sulfamethizole, sulfanilimide (archaic), sulfasalazine, sulfisoxazole, trimethoprim, and trimethoprim-sulfamethoxazole); tetracyclines (such as demeclocycline, doxycycline, minocycline, oxytetracycline, and tetracycline); and others (such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin, thiamphenicol, and tinidazole).

Kits are also provided. In one embodiment, these kits include a container or formulation that contains one or more of the compositions described herein. In one example, this component is formulated in a pharmaceutical preparation for delivery to a subject. The composition is optionally contained in a bulk dispensing container or unit or multi-unit dosage form. Optional dispensing means can be provided. Packaging materials optionally include a label or instruction indicating for what treatment purposes and/or in what manner the pharmaceutical agent packaged therewith can be used.

EXAMPLE

This example describes the determination of peptide inhibitors of $N.$ $gonorrhoeae$ AniA.

Materials and Methods

Bacterial Strains and Growth Conditions. $N.$ $gonorrhoeae$ FA1090 (Connell et al. 1988, Mol Microbiol 2:227-36) was cultured as specified in the text, on gonococcal base solid medium (GCB, Difco) for 18-22 h at 37° C. in the presence of 5% atmospheric $CO_2$ or anaerobically as described previously (Zielke et al. 2016, Mol Cell Proteomics doi: 10.1074/mcp.M116.058800), or in gonococcal base liquid (GCBL) medium supplemented with sodium bicarbonate at a final concentration of 0.042% and Kellogg's supplement I and II in ratios 1:100 and 1:1000; respectively (Spence et al. 2008, Curr Protoc Microbiol Chapter 4:Unit 4A 1). Piliated gonococci were used for DNA transformation, while non-piliated variants were used in all other experiments. $Escherichia$ $coli$ strains were grown either on Luria-Bertani agar (Difco) or cultured in Luria-Bertani broth (Difco) at 37° C.

Antibiotics were used on selected bacteria in the following concentrations: for $N.$ $gonorrhoeae$: kanamycin 40 pg/mL, erythromycin 0.5 pg/mL; for $E.$ $coli$: kanamycin 50 pg/mL, erythromycin 250 pg/m L.

Genetic Manipulations and Site-directed Mutagenesis. Oligonucleotides were designed based on the genomic sequence of $N.$ $gonorrhoeae$ FA1090 (NC_002946) using SnapGene software version 2.8 (GSL Biotech LLC) and synthesized by IDT Technologies. Genomic DNA was isolated with the Wizard Genomic DNA Purification Kit (Promega). PCR products and plasmid DNA were purified using QIAprep Spin Miniprep Kit (QIAGEN). PCR reactions were performed using chromosomal or plasmid DNA as template, appropriate oligonucleotides, and Q5® High-Fidelity DNA Polymerase (NEB). $E.$ $coli$ MC1061 was used as the host during the molecular cloning and site-directed mutagenesis. Obtained constructs were verified by Sanger Sequencing.

Transformation of *N. gonorrhoeae* was performed as described previously (Zielke et al. 2014, Curr Protoc Microbiol 34:1F 3 1-1F 3 16).

The clean deletion of aniA, ΔaniA, was constructed in the *N. gonorrhoeae* FA1090 by in-frame replacement of the aniA (ngo1276) in its native chromosomal locus with the nonpolar kanamycin resistance cassette using a strategy described by Zielke et. al. (Zielke et al. 2016, Mol Cell Proteomics doi:10.1074/mcp.M116.058800). The constructs for deletion of aniA were obtained using Gibson Assembly (Gibson et al. 2009, Nat Methods 6:343-5) as described below. The 1 kb upstream DNA region was amplified using oligonucleotides aniA_up_fwd 5'CCTTAAT-TAAGTCTAGAGTCGCCGGGACGGTTGGTCGA3' (SEQ ID NO: 16) and aniA_up_rev 5'CAGCCTA-CACGCGTTTCAT-AATGTTTTCCTTTTGTAAGAAAAGTAGGG3' (SEQ ID NO: 17) and 1 kb downstream from aniA with primers aniA_down_fwd 5'TAATTCCCATAGCGTTTAT-TAAATCGGATACCCGTCATTAGC3' (SEQ ID NO: 18) and aniA_down_rev 5'GCCTGCAGGTT-TAAACAGTCGGCAAGGCGAGGCAACGC3' (SEQ ID NO: 19). The kanamycin cassette was amplified with oligonucleotides aniA_kan_fwd 5'TAT-GAAACGCGTGTAGGCTGGAGCTGCT3' (SEQ ID NO: 20) and aniA_kan_rev 5'AATAAACGCTATGGGAATT-AGCCATGGTCC3' (SEQ ID NO: 21) using pKD4 as a template. The linearized pNEB193 was obtained by PCR amplification using primers pNEB193_fwd 5'GACTGTT-TAAACCTGCAG3' (SEQ ID NO: 22) and pNEB193_rev 5'GACTCTAGACTTAATTAAGGATCC3' (SEQ ID NO: 23). All fragments were purified, mixed in equimolar proportions and assembled using Gibson Assembly Master Mix. Obtained pNEB193-ΔaniA was linearized with HindIII and introduced into FA1090. Clones were selected on solid medium supplemented with kanamycin and verified by PCR with primers aniA_check_f 5'CTGTCCCATTTT-GAGAGCTCC3' (SEQ ID NO: 24) and aniA_check_r 5'CCTTGTGCGGCGCAATAG3' (SEQ ID NO: 25) and immunoblotting analyses using polyclonal anti-AniA antisera (Zielke et al. 2014, Curr Protoc Microbiol 34:1F 3 1-1F 3 16).

For complementation studies, the wild type aniA allele was amplified with primers aniA_pGCC4_f 5'CTGTTAAT-TAAAAAAGGAAAACATTATCAAACGCC3' (SEQ ID NO: 26) and aniA_pGCC4_r 5'GCTAATGACGGGTATCC-GAT3' (SEQ ID NO: 27). Subsequently, the PCR product was digested with PacI and cloned into PacI/PmeI digested pGCC4 vector under the control of the $P_{lac}$ promoter and introduced onto the chromosome of FA1090 ΔaniA creating ΔaniA/$P_{lac}$::aniA.

To generate a construct for overexpression and purification of mutated, recombinant version of AniA, AniA D137A H280A, site-directed mutagenesis was performed in consecutive reactions using as template pET28-aniA (Zielke et al. 2014, Mol Cell Proteomics 13:1299-317), primer pairs D137A-F 5'CGCACAACGTCGCCTTCCACGCCGCAA3' (SEQ ID NO: 28) D137A-R 5'TTGCGGCGTG-GAAGGCGACGTTGTGCG3' (SEQ ID NO: 29) and H280A-F 5'GAACTTGGTGTCTTCCTTCGCCGT-CATCGGCGAAATCTTC3' (SEQ ID NO: 30) H280A-R 5'GAAGATTTCGCCGATGACGGCGAAGGAAGACAC-CAAGTTC3' (SEQ ID NO: 31), and Q5 Site-Directed Mutagenesis Kit (NEB), per the manufacturer's manual. The presence of mutated sites in obtained pET28-aniAD137A H280A was confirmed by Sanger sequencing.

To generate pGCC4-aniAD137A H280A Gibson assembly method was used to replace wild type aniA with fragment containing mutated sites. The fragment containing mutation was amplified using primers RAZ414 5'GAACCGCCGGCAGGCACGATGGTGCT-GIGTACGTTTTCGTTAATCAG3' (SEQ ID NO: 32) and RAZ415 5'CTACCGCCGAAACGCCTGCAGGCGAACTGCCCG3' (SEQ ID NO: 15) and pET28-aniAD137A H280A as template. Primers RAZ413 5'CGTGCCTGCCGGCGGTTC3' (SEQ ID NO: 33) and RAZ416 5'GCGTTTCGGCGGTAGCTTGTG3' (SEQ ID NO: 34) and plasmid pGCC4-aniA were used to amplify the remaining fragment. Both fragments were gel purified and mixed in equimolar proportions before the Gibson assembly mastermix was added (NEB). The pGCC4-aniAD137A H280A was introduced into the FA1090 ΔaniA chromosome.

Protein Purification. Overproduction of recombinant variants of AniA including wild type protein which lacks the N-terminal palmitoylation signal, sAniA (Zielke et al. 2014, Mol Cell Proteomics 13:1299-317), as well as mutated AniA, D137A H280A, was performed in *Escherichia coli* BL21(DE3) by addition of IPTG to a final concentration of 0.5 mM when the cultures reached an $OD_{600}$ of 0.5. Following 3.5 h incubation, bacteria were pelleted by centrifugation and the pellets were re-suspended in lysis buffer (20 mM HEPES pH 7.5, 500 mM NaCl, 10 mM imidazole) supplemented with a Pierce Protease Inhibitor Mini Tablet (Thermo Scientific). Cells were lysed by passaging five times through a French pressure cell at 12,000 psi. Unbroken cells and cell debris were separated from soluble protein fraction by centrifugation at 16,000×g for 30 min at 4° C. The obtained supernatants were passed through 0.45 μm membrane filter (VWR International) and applied to a nickel affinity column Profinity™ IMAC (Bio-Rad). Columns were washed five times with eight bed volumes of 97:3 of lysis buffer and elution buffer (20 mM HEPES pH 7.5, 500 mM NaCl, 250 mM imidazole), respectively, and proteins were eluted with five bed volumes of elution buffer. Eluates were subjected to dialysis against 20 mM HEPES pH 7.5 supplemented with 0.1 mM cupric chloride dihydrate (EMD Chemicals Inc.) twice for 1 h and subsequently overnight at 4° C. Purified sAniA and AniA D137A H280A proteins were mixed with 10% glycerol and stored at −80° C.

Crystallization, Data Collection, and Structure Solution. Crystallization trial were performed in vapor diffusion hanging drop format using a Mosquito® Crystal robot (TTP Labtech). Crystallization solutions from JSSG Core Suites I-IV (Qiagen) were mixed with the protein solution at three different ratios (0.05 μl protein+0.15 μl crystallization solution; 0.1 μl protein+0.1 μl crystallization solution; 0.15 μl protein+0.05 μl crystallization solution). The initial crystals were harvested without optimization using suitable cryoprotection solutions and flash-cooled in liquid nitrogen. All data were collected at Southeast Regional Collaborative Access Team (SER-CAT) 22-ID beamline at the Advanced Photon Source, Argonne National Laboratory. Data were process and scaled using XDS and XSCALE (Kabsch 2010, Acta Crystallogr D Biol Crystallogr 66:133-44).

A 1.90 Å dataset in space group $P2_12_12_1$ was collected from a single crystal grown in 0.1 M Tris-HCl pH 8.5, 2.0 M ammonium dihydrogen phosphate (JCSG Core II-A11). The crystal was cryoprotected in crystallization solution supplemented with 20% glycerol. Initial phases were determined by molecular replacement using Phaser (McCoy et al. 2007, J Appl Crystallogr 40:658-674) and AniA structure (PDB 1KBV) as a search model (Boulanger and Murphy 2002, J Mol Biol 315:1111-27). The model was re-built using Coot (Emsley et al., 2010, Acta Crystallogr D Biol Crystallogr 66:486-501) and refined using Phenix (Adams et al. 2010, Acta Crystallogr D Biol Crystallogr 66:213-21).

A 2.35 Å dataset in space group /4$_1$22 was collected from a single crystal grown in 0.2 M potassium thiocyanate, 20% PEG3350 (JCSG Core I-C9) and cryoprotected in crystallization solution supplemented with 20% glycerol. The overall completeness of this dataset is 84.8% due to the small crystal size and radiation damage. The structure was solved using Phaser and AniA structure in space group P2$_1$2$_1$2$_1$ (PDB 5TB7) as a search model. The structure was corrected using Coot and refined using Phenix.

The quality of the structures was assessed using Coot and the MolProbity server molprobity.biochem.duke.edu) (Chen et al. 2010, Acta Crystallogr D Biol Crystallogr 66:12-21). The structural superpositions were performed using the Dali server (available on the world wide web at ekhidna2.biocenter.helsinki.fi/dali/) (Holm and Laakso 2016, Dali server update. Nucleic Acids Res 44:W351-5). The structural figures were generated using PyMOL (The PyMOL Molecular Graphics System, Version 1.8 Schrödinger, LLC.).

Immunoblotting. Expression of AniA was assessed in a panel of geographically, temporally and genetically diverse *N. gonorrhoeae* isolates including commonly used laboratory strains FA1090 (Connell et al. 1988, Mol Microbiol 2:227-36), MS11 (Meyer et al. 1982, Cell 30:45-52), 1291 (Apicella et al. 1978, Infect Immun 20:228-34), F62 (Sparling P F. 1966. Genetic transformation of *Neisseria gonorrhoeae* to streptomycin resistance. J Bacteriol 92:1364-71), FA19 (Maness and Sparling 1973, J Infect Dis 128:321-30), the clinical isolates LGB1, LG14, LG20, and LG26, which were collected from two public health clinics in Baltimore from 1991 to 1994 and differ in porB variable region type and pulsed gel electrophoresis patterns (Zielke t al. 2014, Mol Cell Proteomics 13:1299-317; Garvin et al. 2008, Infect Immun 76:3700-9), 13 isolates from patients attending the Public Health—Seattle & King County Sexually Transmitted Disease clinic from 2011 to 2013 (Zielke et al. 2016, Mol Cell Proteomics doi:10.1074/mcp.M116.058800), and the 2016 WHO reference strains (Unemo et al. 2016, J Antimicrob Chemother doi:10.1093/jac/dkw288). All strains were cultured concurrently on solid media for 20 h in 5% $CO_2$ at 37° C., collected from GCB plates and whole-cell lysates were prepared in SDS sample buffer in the presence of 50 mM dithiothreitol, matched by equivalent $OD_{600}$ units and separated in 4-20% Mini-PROTEAN TGX precast gels (Bio-Rad). The immunoblotting analysis was performed using polyclonal rabbit antiserum against recombinant AniA.

Phage display. To identify peptide ligands interacting with AniA, two M13-based phage libraries, Ph.D. C7-C and Ph.D.-12 (New England BioLabs) were used in biopanning experiments following procedures described in a study reporting identification of peptide inhibitors targeting *Clostridium difficile* toxins A and B (Abdeen et al. 2010, ACS Chem Biol 5:1097-103). Magnetic Ni-NTA bead-based affinity capture was used to immobilize sAniA. A preclearance step was included prior to each round of biopanning to remove $Ni^{2+}$ and plastic binders from the phage pool (Abdeen et al. 2010, ACS Chem Biol 5:1097-103; Molek et al. 2011, Molecules 16:857-87). The phages from each library ($10^{10}$ pfu/mL) were incubated with magnetic Ni-NTA agarose beads (250 pg capacity) at RT for 1 h. The supernatants of this solution provided the precleared phage pool. For target immobilization, Ni-NTA beads (50 pg capacity) were coated with 100 pg of sAniA. Unbound sAniA was washed away and the precleared phage pool was added. Following incubation, unbound phages were removed by washing 20 times with TBST. Three rounds of biopanning were performed with increasing specificity obtained by raising the Tween concentration from 0.1% in the first biopanning experiment to 0.5% in the subsequent two rounds during washing step (El Zoeiby et al. 2003, J Antimicrob Chemother 51:531-43; Paradis-Bleau et al. 2008, BMC Biochem 9:33). Elution of phages was performed with 0.2 M glycine-HCl (pH 2.2). At the end of each round of selection, eluted phages were titrated and amplified in *E. coli* ER2738 (NEB) per the manufacturer's protocol. After the third round, 24 phage colonies from each library were selected randomly. Phage DNA was purified as recommended in the manufacturer's protocol (NEB) and sequenced using 96 gIII sequencing primer 5"CCCTCATAGTTAGCGTAACG3" (SEQ ID NO: 35).

Phage Enzyme-linked Immunosorbent Assay (Phage ELISA). Individual wells in 96-well transparent plates (Greiner-Bio) were coated with 100 μL of 100 μg/mL of sAniA suspended in 0.1 M $NaHCO_3$ pH 8.6 and incubated overnight at 4° C. in an airtight humidified box. After incubation, excess target solution was shaken out and wells were filled with 300 μL of blocking buffer (0.1 M $NaHCO_3$ pH 8.6, 5 mg/mL BSA). Following 2 h incubation at 4° C., blocking buffer was removed and wells were washed six times with 200 μL of TBST (50 mM Tris-HCl pH 8.6, 150 mM NaCl, 0.5% Tween). Isolated individual phage amplifications ($10^{10}$ PFU) in 100 μl of TBST were incubated at room temperature for 1 h with rocking. All wells were then cleared by shaking and washed six times with 200 μL of TBST. A solution containing Anti-M13 HRP linked-Monoclonal Antibodies (NEB) (1:5,000 dilution in blocking buffer) was distributed at 200 μL per well and incubated with rocking at room temperature for 1 h. Wells were washed six times with TBST and incubated with Turbo TMB-ELISA for 30 min with rocking at room temperature. To stop the reaction, finally 100 μL of 1.78 M $H_2SO_4$ was added to each well. A Synergy HT plate reader (BioTek) measured color intensity and readings were compared to control wells, which underwent identical treatment but lacked sAniA (designated as control) and to signal from wild type infectious virions that do not display peptides, M13KE, ($10^{10}$ PFU; designated as wild type) derived from the PhD cloning vector (NEB). Data from seven independent experiments are shown with mean and SEM Measurements of Nitrite Reductase Activity with Purified AniA Variants. Enzymatic activity assessments with sAniA and AniA D137A H280A were performed based upon previous work (Boulanger and Murphy 2002, J Mol Biol 315:1111-27; Kakutani et al. 1981, J Biochem 89:463-72) but using a highly sensitive fluorometric assay for nitrite measurements that relies on the reaction of nitrite with 2,3-diaminonapthalene (DAN) to form the fluorescent product, 1-(H)-naphtothriazole (Misko et al. 1993, Anal Biochem 214:11-6). All reactions were conducted under anoxic or microoxic conditions. Fluorescence was measured at excitation of 360/40 nm and emission of 460/40 nm at a gain of 50 using a Synergy HT Plate Reader (BioTek). The sAniA and AniA D137A H280A activities are expressed as the mean reaction rate (nmoles of nitrite reduced/min/pg protein) from at least ten independent experiments over the course of a nitrite utilization assay (Shewell et al. 2013, Biochem Biophys Res Commun 431:215-20).

Determination of Peptides Inhibitory Concentrations Required to Reduce the Signal by 50% ($IC_{50}$s). Synthetic peptides 12-5 (H-KHYYGGDTTTLWGGGS-NH$_2$(SEQ ID NO: 1)), C7-3 (H-ACNYCRLNLWGGGS-NH$_2$ (SEQ ID NO: 2)), C7-3m1 (H-ACNYSRLNLWGGGS-NH$_2$ (SEQ ID NO: 3)), C7-3m2 (H-ACSYCRLNLWGGGS-NH$_2$ (SEQ ID NO: 4)), C7-3P (H-ACNFCRLNLWGGGS-NH$_2$ (SEQ ID NO: 5)), C7-3A (H-ACNACRLNLWGGGS-NH$_2$(SEQ ID NO: 6)), and C7-3Bio, biotinylated at the N-terminus version of C7-3 (BiotinAhx-ACNYCRLNLWGGGS-NH$_2$ (SEQ ID NO: 2)) were acquired from Pepmic Co., dissolved in ddH$_2$O or dimethylformamide and serially diluted before addition to sAniA (1 μM). Nitrite measurements with DAN were performed as described above after pre-incubation of samples for 1 h at room temperature. Control reactions consisted of sAniA alone and AniA D137A H280A treated in the same manner as the experimental samples. Reactions were performed in at least twelve independent experiments. Percent inhibition was calculated using the formula % I=100*(1−(x−y)/(z−y)) where "x", "y" and "z" are the concentrations of nitrite in samples containing sAniA incubated with synthetic peptides, AniA D137A H280A and sAniA, respectively. The data were analyzed with a nonlinear log(inhibitor) vs. response—variable slope (four parameters) curve-fitting technique (GraphPad) to obtain 1050 values. All experiments were performed in at least ten independent trials.

Whole Cell Nitrite Utilization Studies. The FA1090 ΔaniA/P$_{lac}$::aniA and ΔaniA/P$_{lac}$::D137AH280A were grown to OD$_{600}$~1.0, gently spun down, decanted and re-suspended in GCBL. Cell suspensions were incubated in the absence or presence of synthetic peptides 12-5, C7-3, C7-3m1, and C7-3m2 (0.15, 0.3, and 0.6 mM) at 37° C. for 30 min. Subsequently, 0.1 mM sodium nitrite was added and the samples were transferred into an anaerobic chamber. After 1 h, nitrite consumption was measured using Griess Reagent (Biotium) as previously described for *N. gonorrhoeae* nitrite reductase whole cell assay (Shewell et al. 2013, Biochem Biophys Res Commun 431:215-20). Absorbance values were measured at OD$_{545}$ using a Synergy HT plate reader and nitrite concentration was assessed against a nitrite standard prepared in GCBL. Percent inhibition was calculated using the formula % 1=100*(1−(x−y)/(z−y)) where "x", "y" and "z" are the concentrations of nitrite in samples containing FA1090 ΔaniA/P$_{lac}$aniA incubated with synthetic peptides, ΔaniA/P$_{lac}$aniA D137A H280A and ΔaniA/P$_{lac}$aniA, respectively. Experiments were performed on at least three separate occasions and mean with SEM are reported.

Open State of the AniA Homotrimer Structure. Normal Modes Analysis (NMA) is a method for characterizing motions of macromolecules based on basis vectors (normal modes), which describes the flexibility of the molecule (Tirion 1996, Phys Rev Lett 77:1905-1908; Hinsen 1998, Proteins-Structure Function and Genetics 33:417-429; Ma 2004, Current Protein & Peptide Science 5:119-123). The visual inspection of the 20 lowest frequency normal modes computed by the elNémo server showed that the first four lowest frequencies of the normal mode of vibrations corresponded to the largest amplitude motions of the extended and collapsed conformations of the AniA structure (Suhre and Sanejouand 2004, Nucleic Acids Res 32:W610-4; Suhre Sanejouand 2004, Acta Crystallogr D Biol Crystallogr 60:796-9). Therefore, these modes were used for generating alternative conformational transition of the protein. To generate alternate conformations of AniA, we started from the structure of AniA in P2$_1$2$_1$2$_1$ space group (PDB 5TB7) and displaced the protein along the subspace defined by the first low frequency mode. Such movements were made to generate a more extended state transition (conformation) of the whole structure. Next, the resulting protein conformation defined by the amplitude of variation was energy-minimized. The resulting structure was then submitted to the elNémo server, the normal modes were computed, and the protein was displaced again using the second lowest new normal mode. This process was repeated until the protein structure was opened using the fourth lowest normal mode.

Molecular Modeling of the Binding Peptide with AniA. The multiple conformational states of the peptides were generated using OMEGA (Open Eye Scientific Software) and MD simulations (Hawkins and Nicholls 2012, J Chem Inf Model 52:2919-36). The docking poses of the multi-conformations of peptide structures (ligands) were performed using 4Dshape+software [Chem Design Solutions LLC, (Wei and Hamza 2014, J Chem Inf Model 54:338-46; Hamza et al 2014, J Chem Inf Model 54:2834-45)]. The docking strategy exhaustively docked/scored all possible positions of each ligand (each peptide conformation) in the AniA binding site. The rigid docking roughly consisted of two steps—shape fitting and application of optimization filters. During the shape fitting, the ligand (peptide structure) was placed into a 0.5 Å resolution grid box encompassing all active-site atoms (including hydrogen atoms) using smooth Gaussian potential. Two optimization filters were subsequently processed—rigid-body optimization and optimizatiowen of the ligand pose in the dihedral angle space. The pose ensemble was filtered to reject poses that did not have sufficient shape complementarity with the active site of the protein. In separate docking runs, the binding poses of the ligand structure were refined by MD simulations followed by free energy calculations using Sander module from Amber12 package (Case et al. 2012, AMBER 12. San Francisco, Calif.: University of California) as previously described (Hamza et al 2014, J Chem Inf Model 54:1166-1173; Zhou et al. 2013, J Nat Prod 76:279-286; Zhang et al. 2013, ACS Chem Biol doi:10.1021/cb3005353; Hamza et al. 2011, Bioorg Med Chem 19:6077-6086). The AniA-peptide binding complex was neutralized by adding appropriate counter ions and was solvated in a rectangular box of TIP3P water molecules with a minimum solute-wall distance of 10 Å. (Jorgensen 1981, J Am Chem Soc 103:335-340) The solvated systems were energy-minimized and carefully equilibrated. These systems were gradually heated from T=10 K to T=298.15 K in 50 ps before running an MD simulation. The MD simulations were performed with a periodic boundary condition in the NPT ensemble at T=298.15 K with Berendsen temperature coupling and constant pressure (P=1 atm) with isotropic molecule-based scaling. A time step of 2.0 fs was used, with a cutoff of 12 Å for the nonbonded interactions, and the SHAKE algorithm was employed to keep all bonds involving hydrogen atoms rigid (Ryckaert et al. 1977, Journal of Computational Physics 23:327-341) Long-range interactions were handled using the particle mesh Ewald (PME) algorithm (Darden et al. 1993, J Chem Phys 98:10089-10092). During the energy minimization and MD simulations, only the ligand (peptide) and residue side chains in the binding pocket were permitted to move. This constraint was used to prevent any changes in the AniA structure due to the presence of residues in the loops on the top of the protein active site. A residue-based cutoff of 12 Å was utilized for non-covalent interactions. MD simulations were then carried out for ~10.0 ns. During the simulations, the coordinates of the system were collected every 1 ps. The last 20 snapshots of the simulated structure of the MD trajectory were used to perform the binding free energy calculations.

Binding Free Energy Calculation. The obtained stable MD trajectory for each AniA-peptide complex was used to estimate the binding free energy ($\Delta G_{bind}$) by using the Sietraj program (Naim et al. 2007, J Chem Inf Model 47:122-133). The program calculates the solvated interactions energies (SIE) using five terms and three parameters that were fitted to reproduce the binding free energies of a data set of 99 ligand protein complexes by Naim et al (Naim et al. 2007, J Chem Inf Model 47:122-133). The Sietraj is a substitute of molecular mechanism/Poisson-Boltzmann surface area (MM/PBSA) method (Kollman et al. 2000, Acc Chem Res 33:889-897).

Biolayer Interferometry. The binding affinity of C7-3Bio, biotinylated C7-3 peptide (BiotinAhx-ACNYCRLNLWGGGS-NH$_2$ (SEQ ID NO: 2)) to sAniA was assessed by biolayer interferometry on an OctetRed 96 (ForteBio, Menlo Park, Calif.). The C7-3 was dissolved first in dimethylformamide to a final concentration of 1.2 mM and finally in Kinetic Buffer (ForteBio) to a final concentration of 20 µg/mL. Streptavidin (SA) biosensors (ForteBio) were loaded with C7-3Bio peptides for 10 min. Unloaded tips were used as a control. The sAniA samples were prepared in Kinetic Buffer in concentrations of 50, 100, 500, and 1000 nM. The baseline was established for 240 s and the association and dissociation steps were performed for 500 s. Experiments were performed in three biological replicates with the curve fitting using 2:1 (Heterogeneous Ligand) model and K$_D$ value calculations were completed using Octet Data Analysis (version 9).

Results

Refining the *N. gonorrhoeae* AniA Structure. The structure of *N. gonorrhoeae* AniA has been reported (Boulanger and Murphy 2002, J Mol Biol 315:1111-27). However, the high ionic strength in the crystallization condition of AniA in space group P1 (Boulanger and Murphy 2002, J Mol Biol 315:1111-27). is not readily suitable for co-crystallization with inhibitors. To facilitate the targeting of AniA with small molecule inhibitors, the recombinant version of AniA, sAniA (Zielke et al. 2014, Mol Cell Proteomics 13:1299-317), from *N. gonorrhoeae* strain FA1090 was purified and the new structures of the *N. gonorrhoeae* AniA were solved and refined to 1.90 Å and 2.35 Å resolution in two novel crystal forms, $P2_12_12_1$ and $I4_122$, respectively (Table 1 and FIG. 1 B-D).

TABLE 1

Data collection and refinement statistics.

|  | AniA (PDB 5TB7) | AniA (PDB 5UE6) |
|---|---|---|
| Data collection |  |  |
| Wavelength (Å) | 1.0000 | 1.0000 |
| Space group | $P2_12_12_1$ | $I4_122$ |
| Cell dimensions: |  |  |
| a, b, c (Å) | 76.23, 129.10, 136.72 | 177.34, 177.34, 449.46 |
| α, β, γ (°) | 90, 90, 90 | 90, 90, 90 |
| Resolution (Å) | 66.58-1.90 (1.95-1.90)[a] | 83.68-2.35 (2.41-2.35) |
| $R_{sym}$ | 0.090 (1.038) | 0.179 (1.050) |
| $CC_{1/2}$[b] | 99.8 (67.7) | 99.0 (75.4) |
| I/σI | 11.7 (1.9) | 5.8 (1.8) |
| Completeness (%) | 99.2 (100) | 84.8 (83.3) |
| Multiplicity | 6.2 (6.3) | 4.2 (3.9) |
| Refinement |  |  |
| Resolution (Å) | 66.58-1.90 | 83.68-2.35 |
| No. reflections (total/free) | 105946/10240 | 125511/11871 |
| $R_{work}/R_{free}$ | 0.155/0.179 | 0.236/0.259 |
| Number of atoms: |  |  |
| Protein | 7156 | 21242 |
| Ligand/ion | 21 | 27 |
| Water | 486 | 984 |
| B-factors: |  |  |
| Protein | 34.1 | 37.2 |
| Ligand/ion | 53.7 | 36.5 |
| Water | 41.9 | 32.2 |
| All atoms | 34.6 | 36.1 |
| Wilson B | 37.4 | 31.7 |
| R.m.s. deviations: |  |  |
| Bond lengths (Å) | 0.010 | 0.003 |
| Bond angles (°) | 1.006 | 0.638 |
| Ramachandran distribution[c] (%): |  |  |
| Favored | 98.7 | 98.2 |
| Outliers | 0 | 0 |
| MolProbity score[d] | 0.71 | 0.79 |

[a]Values in parentheses are for the highest-resolution shell.
[b]$CC_{1/2}$ correlation coefficient as defined in Karplus & Diederichs (Karplus and Diederichs 2012, Science 336: 1030-3) and calculated by XSCALE (Kabsch 2010, Acta Crystallogr D Biol Crystallogr 66: 125-32).
[c]Calculated using the MolProbity server (available on the world wide web at molprobity.biochem.duke.edu) (Chen et al. 2010, Acta Crystallogr D Biol Crystallogr 66: 12-21).
[d]MolProbity score combines the clashscore, rotamer, and Ramachandran evaluations into a single score, normalized to be on the same scale as X-ray resolution Chen et al. 2010, Acta Crystallogr D Biol Crystallogr 66: 12-21).

While the crystals belonging to P2₁2₁2₁ form were grown from the high ionic strength condition, the crystals belonging to /4₁22 form were obtained using 0.2 M potassium thiocyanate and 20% PEG3350 crystallization solution. Therefore, the /4₁22 crystals should be readily amenable for co-crystallization or soaking experiments with potential inhibitors or small molecule fragments. The C-terminal residues 355-363, which have not been modeled in the previous AniA structure (Boulanger and Murphy 2002, J Mol Biol 315:1111-27), form an additional β-strand that reaches over to the neighboring subunit and engages in inter-subunit β-strand complementation. Interestingly, similar inter-subunit interactions have been observed in the structures of other bacterial nitrite reductases, for example from *Alcaligenes faecalis* (Murphy et al. 1997, J Biol Chem 272:28455-60), *Achromobacter xylosoxidans* (Ellis et al. 2001, Acta Crystallogr D Biol Crystallogr 57:1110-8), *A. cycloclastes* (Liu et al. 2003, Biochem Biophys Res Commun 302:568-74). Otherwise, the AniA structures are similar to the previously determined AniA structure (Boulanger and Murphy 2002, J Mol Biol 315:1111-27), with 0.3 Å r.m.s.d. between individual subunits (FIG. 1 B-C).

*N. gonorrhoeae* AniA is a timer with each monomer consisting of two β-sandwich cupredoxin domains (FIG. 1). The monomers contain two types of Cu-binding sites involved in catalysis. The type 1 Cu site is coordinated by Cys125, Met188, His134 and His183 residues from the same subunit. The type 2 Cu site is located in the interface between subunits and is coordinated by His139 and His174 residues from one subunit and His329 residue form another subunit. Interestingly, another His residue—His280—is located in vicinity of the type 2 Cu site, but does not directly coordinates the Cu ion.

Figure 7:
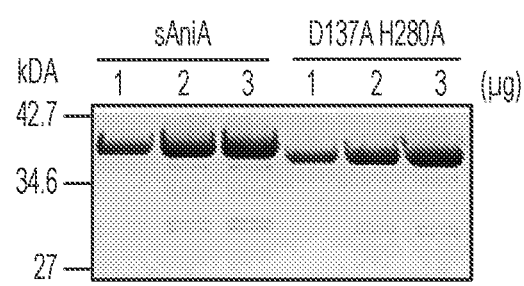
FIG. 7 illustrates the gene encoding AniA (NGO1276) lacking the N-terminal palmitoylation signal was amplified, cloned and purified using Ni-NTA chromatography, sAniA. A site directed mutagenesis approach has been utilized to alter the catalytic residues into alanine. The resulting mutated version of AniA, D137A H280A, containing a C-terminal 6xHis tag was purified using Ni-NTA chromatography. Different amounts of purified proteins, as indicated, were separated by SDS-PAGE and stained with Colloidal Coomassie Blue G-250.

The Nitrite Reductase Function of AniA is Pivotal for *N. gonorrhoeae* Survival Under Anaerobic Conditions. The insertional mutation within aniA locus caused loss of *N. gonorrhoeae* viability under anaerobic growth conditions (Mellies et al. 1997, Mol Gen Genet 256:525-32; Cardinale and Clark 2000, Infect Immun 68:4368-9). Corroborating these findings, in frame aniA deletion knockout in the FA1090 background, ΔaniA, grew robustly aerobically but no colonies were observed under oxygen-limited conditions (FIG. 1 E). To test whether this effect on gonococci viability is associated with nitrite reductase function of AniA, a mutated version of the enzyme with altered predicted catalytic residues D137A H280A [FIG. 1 and (Boulanger and Murphy 2002, J Mol Biol 315:1111-27)] was created using site-directed mutagenesis. Subsequently, the wild type aniA allele and aniA D137A H280A were cloned under the control of $P_{lac}$ promoter and introduced individually onto chromosome of FA1090 ΔaniA creating ΔaniA/$P_{lac}$::aniA and ΔaniA/$P_{lac}$::aniA D137A H280A, respectively. Bacterial suspensions of the same optical density were spotted on GCB containing nitrite as terminal electron acceptor and IPTG to induce expression of aniA. Under aerobic conditions all strains grew similarly to the wild type *N. gonorrhoeae* and full complementation of ΔaniA phenotype was achieved in ΔaniA/$P_{lac}$::aniA incubated anaerobically. In contrast, ΔaniA/$P_{lac}$::aniA D137A H280A failed to form colonies under oxygen-limited conditions, demonstrating that nitrite reductase function of AniA is critical for *N. gonorrhoeae* survival during anaerobiosis (FIG. 1 E). To assess enzymatic activities of sAniA and AniA D137A H280A, both recombinant proteins were purified in milligram quantities to homogeneity (FIG. 7) and subjected to the measurement of nitrite utilization in a fluorometric assay (Boulanger and Murphy 2002, J Mol Biol 315:1111-27; Kakutani et al. 1981, J Biochem 89:463-72; Misko et al. 1993, Anal Biochem 214:11-6; Kakutani et al. 1981, J Biochem 89:453-61). The enzymes were individually incubated with nitrite as the substrate, and dithionate-reduced methyl viologen as an artificial electron donor. Following incubation, the reactions were stopped and the concentrations of residual nitrite were determined with the DAN reagent (Misko et al. 1993, Anal Biochem 214:11-6). As shown in FIG. 1 F, the wild type protein, sAniA, consumed nitrite in a dose dependent manner, whereas the mutated version of AniA, AniA D137A H280A, displayed completely abolished nitrite reductase activity.

Together, these studies demonstrated importance of the predicted catalytic residues D137 and H280 in the enzymatic function of AniA and gonococci viability under anoxia.

Figure 2:
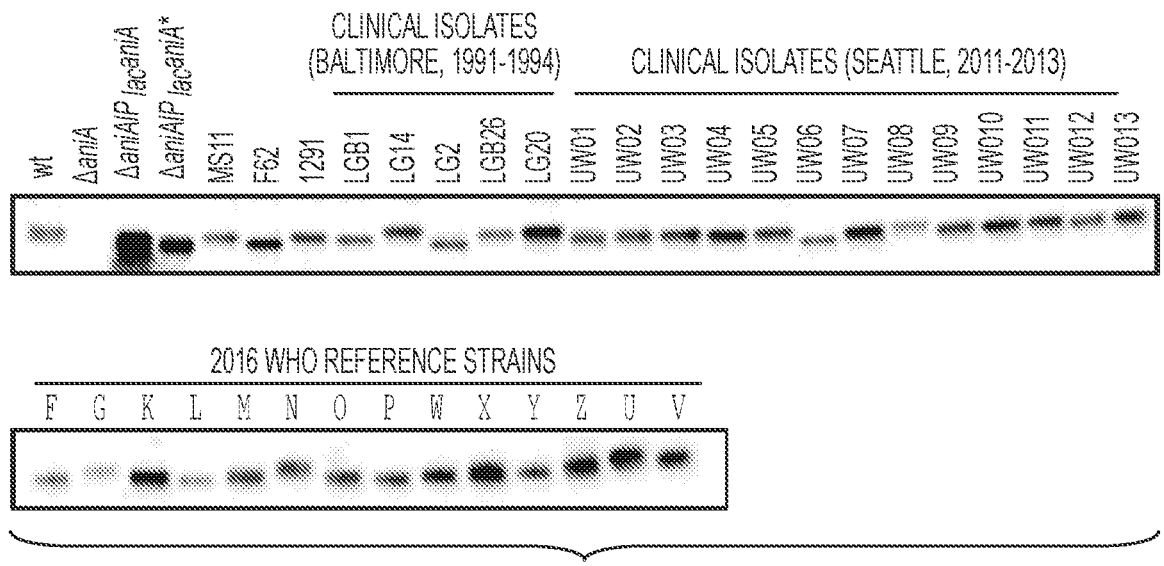
FIG. 2 shows AniA is expressed in a diverse panel of *N. gonorrhoeae* isolates. *N. gonorrhoeae* wild type FA1090, isogenic $\Delta$aniA/$P_{lac}$::aniA and $\Delta$aniA/$P_{lac}$::aniAD137A H280A, as well as 36 additional strains of *N. gonorrhoeae*, as indicated above the immunoblot, were grown concurrently on solid media for 20 h in 5% $CO_2$ at 37° C. Strains $\Delta$aniA/$P_{lac}$::aniA and $\Delta$aniA/$P_{lac}$::aniAD137A H280A were grown on solid media supplemented with IPTG. Samples containing the whole-cell lysates were matched by equivalent $OD_{600}$ units, resolved in 4-20% Tris-glycine gel, and transferred onto nitrocellulose. The immunoblotting was performed using polyclonal rabbit antiserum against sAniA.
Figure 8A:
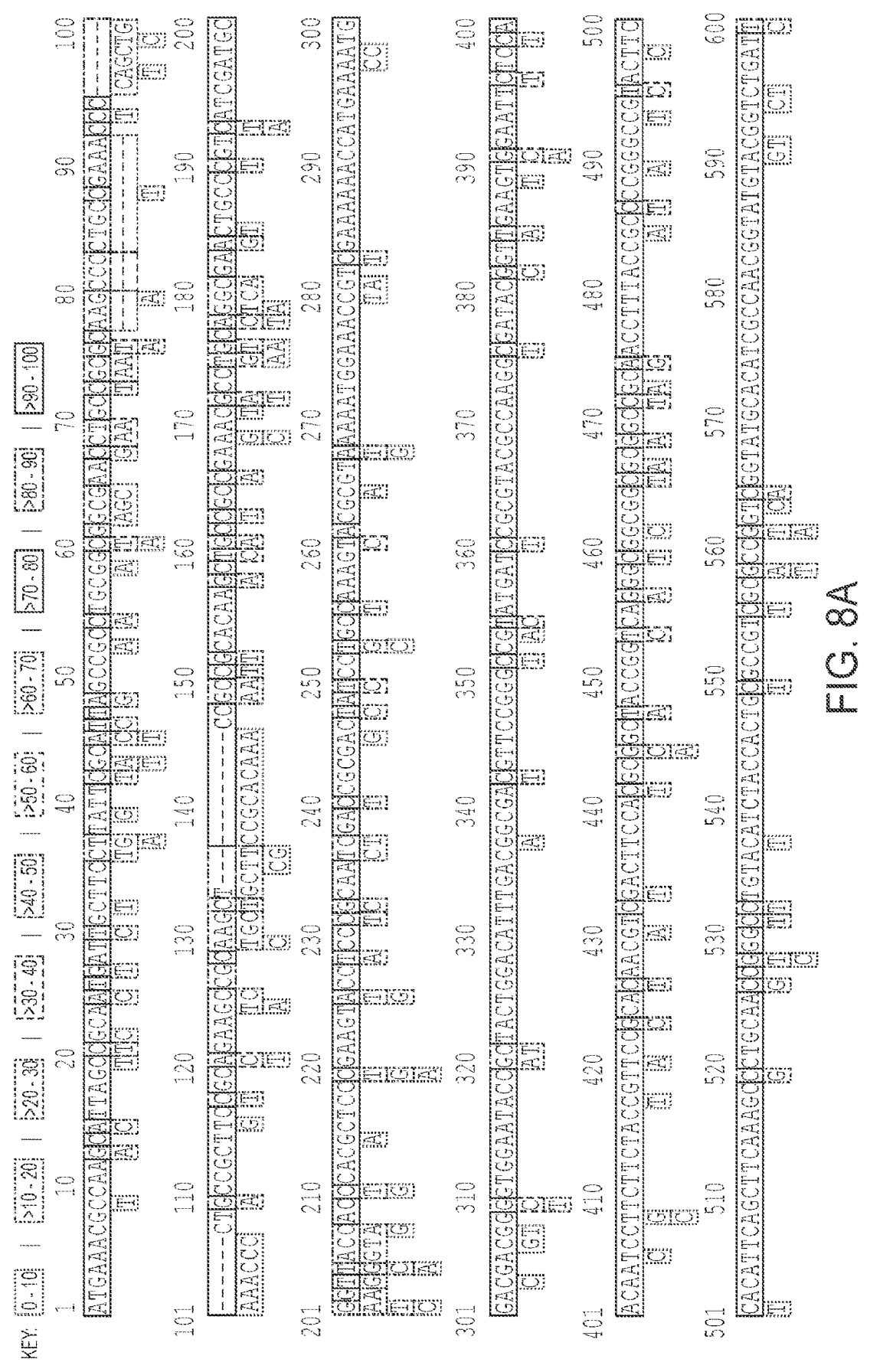
Figure 8B:
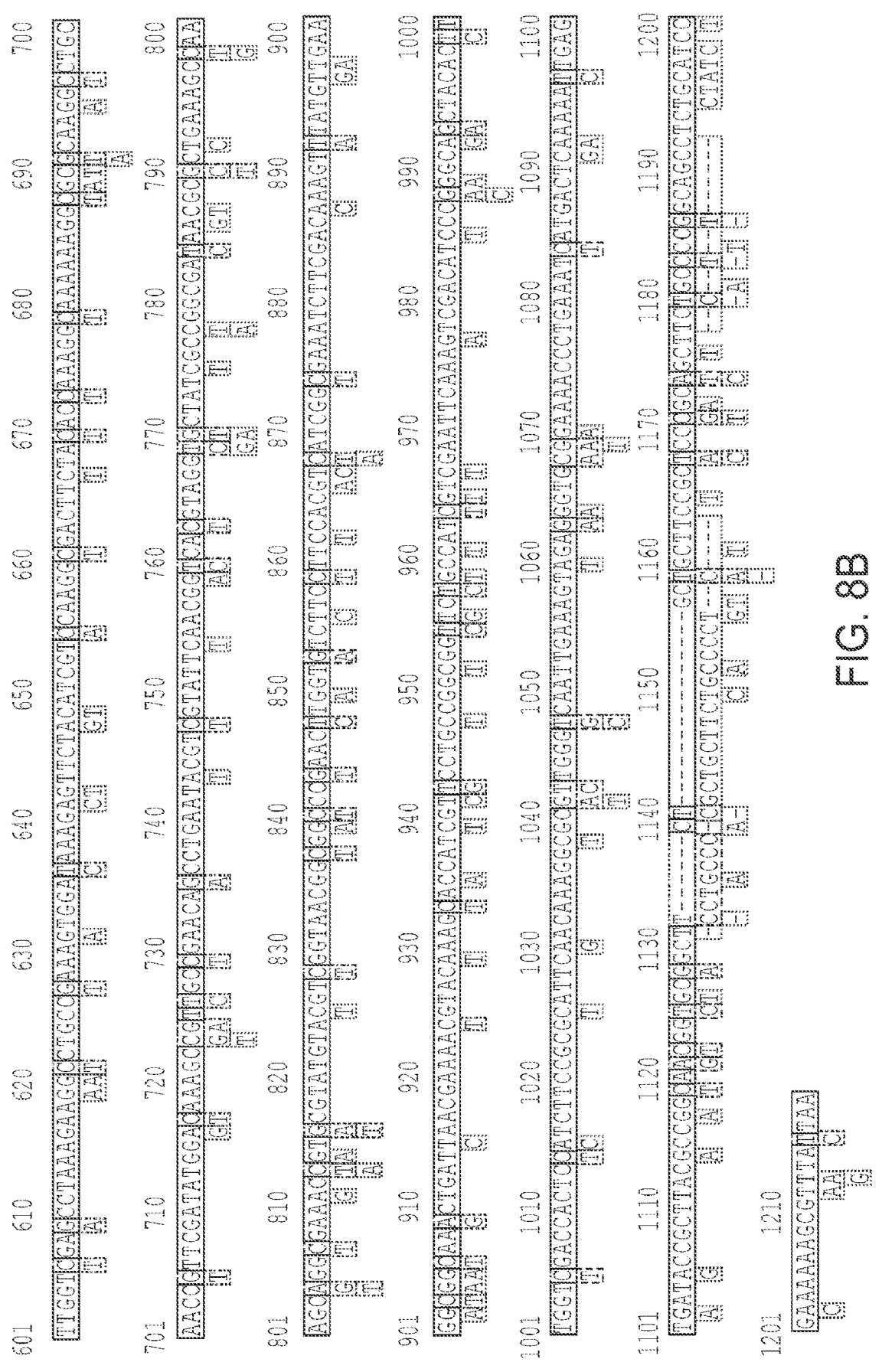

AniA is Expressed in a Panel of Geographically, Temporally and Genetically Diverse Gonococcal Isolates. AniA appeared as one of the major anaerobically induced outer membrane protein that was not detected under aerobic growth (Zielke et al. 2016, Mol Cell Proteomics doi: 10.1074/mcp.M116.058800; Clark et al. 1987, Infect Immun 55:1359-64). We, however, have shown that four different laboratory isolates of *N. gonorrhoeae* cultured under standard aerobic conditions as well as in the presence of normal human sera and during iron deprivation had sufficient amounts of AniA not only to be detectable by mass spectrometry but also by standard immunoblotting (Zielke et al. 2016, Mol Cell Proteomics doi:10.1074/mcp.M116.058800; Zielke et al. 2014, Mol Cell Proteomics 13:1299-317). Analysis of aniA conservation (FIG. 8) demonstrated existence of 318 alleles with 395 single nucleotide polymorphic sites present in the 42,088 isolates of *Neisseria* spp. deposited into the PubMLST database (available on the world wide web at pubmlst.org/neisseria/ as of Jan. 25, 2017). Further, expression of aniA was tested in whole cell lysates derived from aerobically grown 36 different *N. gonorrhoeae* strains isolated from patients at different times and geographic locations, including the 2016 WHO reference strains (Unemo et al. 2016, J Antimicrob Chemother doi:10.1093/jac/dkw288), by SDS-PAGE and immunoblotting with polyclonal anti-AniA antisera (Zielke et al. 2014, Mol Cell Proteomics 13:1299-317). Antisera against AniA cross-reacted with all clinical isolates, albeit, there were noticeable differences in AniA levels between the strains (FIG. 2).

The conservation and expression of AniA during different growth conditions and among diverse gonococci further highlights the importance of maintenance of this outer membrane protein in *N. gonorrhoeae*.

Figure 3A:
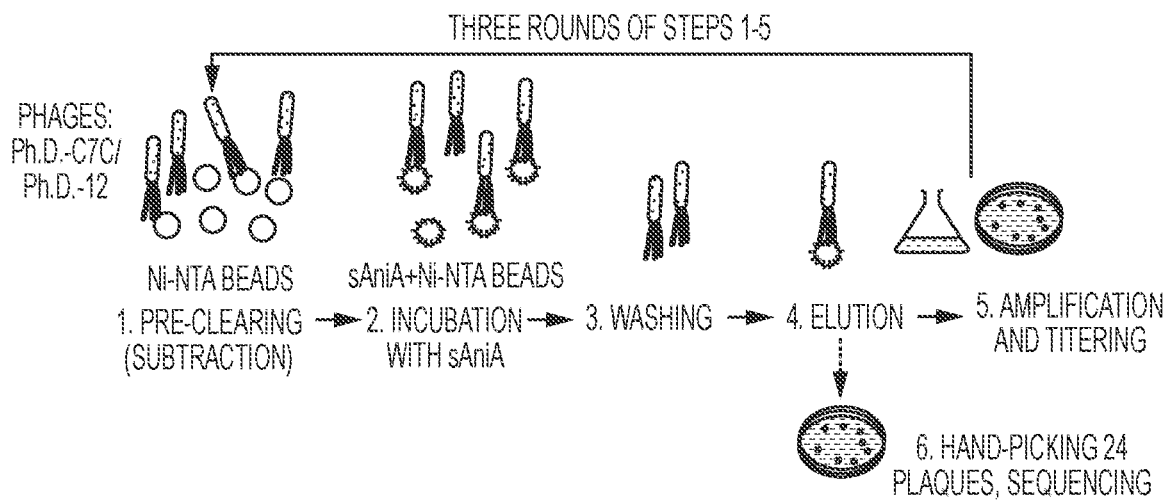

Targeting AniA Using a Phage Display Approach. A phage display approach was chosen to identify peptide ligands interacting with AniA as this technology has been successfully applied in basic and translational research and some of the identified peptides are currently in preclinical or clinical trials (Huang et al. 2012., Antimicrob Agents Chemother 56:4569-82; Fjell et al. 2012, Nat Rev Drug Discov 11:37-51). To provide high diversity of the peptide sequences, two commercially available M13-phage based randomized peptide libraries comprised of $1.9 \times 10^9$ independent linear dodecameric peptides (Ph.D-12) and $3.7 \times 10^9$ heptameric peptides each flanked by a pair of cysteine residues (Ph.D-C7C) were used (FIG. 3). An affinity capture method was used by immobilizing sAniA onto magnetic Ni-NTA agarose and, as outlined in FIG. 3, pre-clearing steps prior to each of biopanning experiments to remove Ni-NTA- and plastic-binding sequences. Simultaneously, increasing stringency during washing at consecutive three rounds of biopanning experiments was applied. Finally, the DNA of 24 randomly chosen phages from each group was extracted and sequenced. The total of 29 different deduced peptide sequences were identified with 6 and 23 different peptides in the Ph.D-C7C and Ph.D-12 phages pool, respectively. Strikingly, one heptameric peptide, designated as C7-3 (CNYCRLNLW (SEQ ID NO: 7)), was identified 19 times (FIG. 3 B).

The ability of binding the phage-displayed peptides to sAniA was subsequently examined in monoclonal phage ELISA. The 29 phage clones, $10^{10}$ PFU per each well, were individually incubated in sAniA-coated wells of microtiter plates. Following extensive washing the signal was detected by monoclonal anti-M13 HRP-conjugate coupled with a colorimetric reaction (FIG. 3 C). These studies revealed C7-3 and 12-5 (KHYYGGDTTTLW (SEQ ID NO: 8)) as the best binding among heptameric and dodecameric phage-expressed peptides, respectively, and these two peptides were selected for further investigations.

Figure 4:
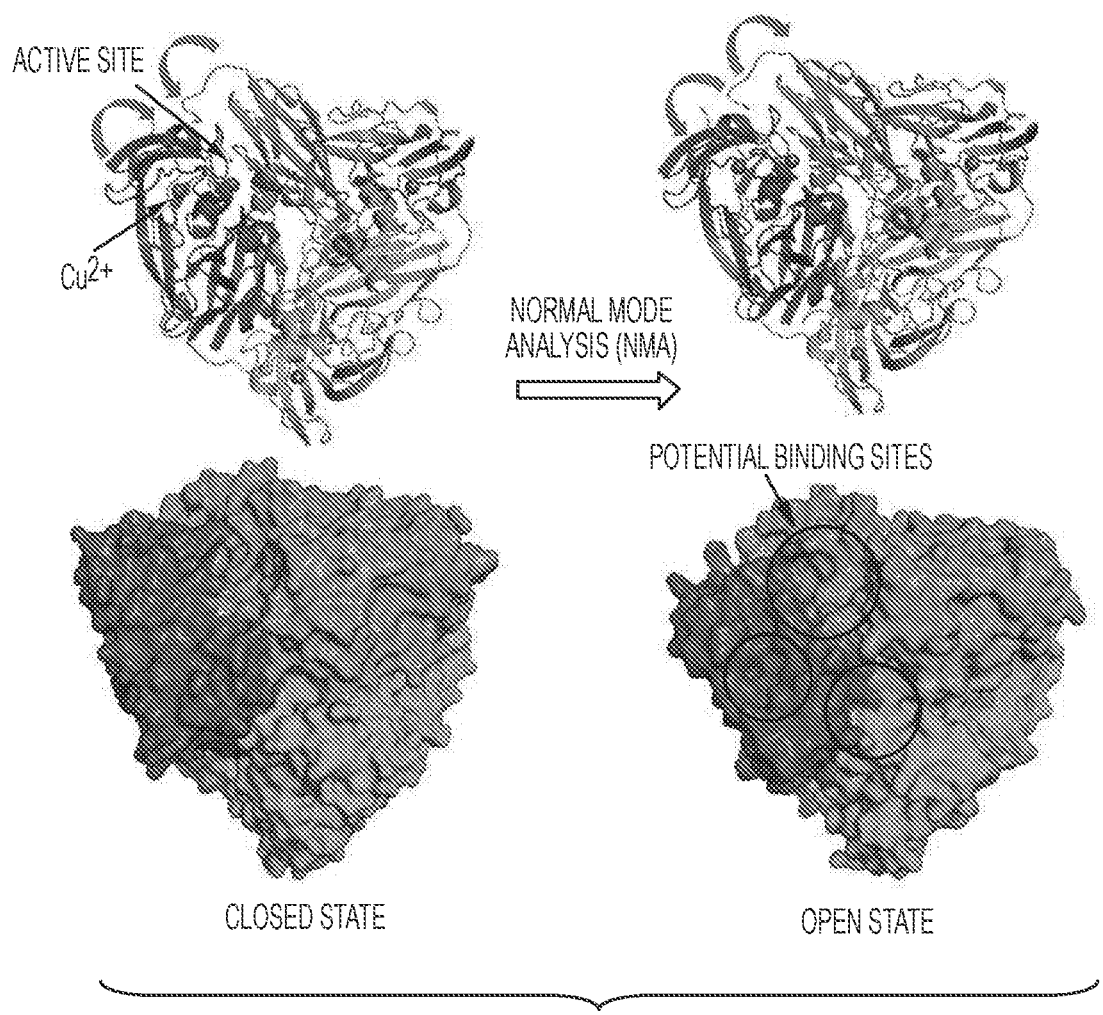
FIG. 4 shows the Normal Mode Analysis (NMA) of the conformational transition of the homotrimer AniA structure. The motion of the combined four lowest normal modes of vibrations described the opening and closing state of the cupredoxin domain II ($Cu^{2+}$ catalytic active site) of the AniA structure. Thus, NMA revealed the tendency of the protein to move in a certain direction even though this movement is not fully explored during the MD simulations. The view on the top of the catalytic active site of AniA structure shows that the flexibility of the protein is well oriented and can dramatically change the accessible area of the catalytic metal ion $Cu^{2+}$ and its potential interaction with a ligand ($NO_2$ or peptide). The open state of the homotrimer AniA structure was used to identify several binding pockets. These conformations depended essentially on the residues sequence composing the peptide. Afterward, the initial conformation of the peptide (stable conformation in the solvent) was slightly perturbed during the docking procedure due to the interactions with the receptor.

Docking Studies. It has been observed that NMA is well suited for describing conformational changes between bound and unbound (apo) protein structures (Petrone and Pande 2006, Biophys J 90:1583-1593; Stambouli et al. 2014, J Biomol Struct Dyn 32:1202-10; Wei et al. 2013, J Biomol Struct Dyn 31:841-53). To understand AniA-peptide interactions, it was critical to determine the flexibility and the conformational states of the homotrimer AniA structure. Whereas in the standard MD simulation all atoms of the protein are of equal importance, in this approach the structural flexibility of the protein conformation was linear combinations of the lowest normal mode of vibrations. Thus, the total molecular flexibility was approximated by considering only the most significant degrees of freedom (Wei et al. 2012, Journal of Biomolecular Structure and Dynamics doi:10.1080/07391102.2012.713781:1-13; Stambouli et al. 2013, Journal of Biomolecular Structure and Dynamics doi:10.1080/07391102.2013.819297:1-9). As shown in FIG. 4, the motion of the combined four lowest normal modes of vibrations described the opening and closing state of the cupredoxin domain II ($Cu^{2+}$ catalytic active site) of the AniA structure. Thus, NMA revealed the tendency of the protein to move in a certain direction even though this movement was not fully explored during the MD simulations.

The view on the top of the catalytic active site of AniA structure (FIG. 4) shows that the flexibility of the protein is well oriented and can dramatically change the accessible area of the catalytic metal ion $Cu^{2+}$ and its potential interaction with a ligand ($NO_2$ or peptide). The open conformation of the homotrimer AniA structure was used to identify several binding pockets.

Figure 5:
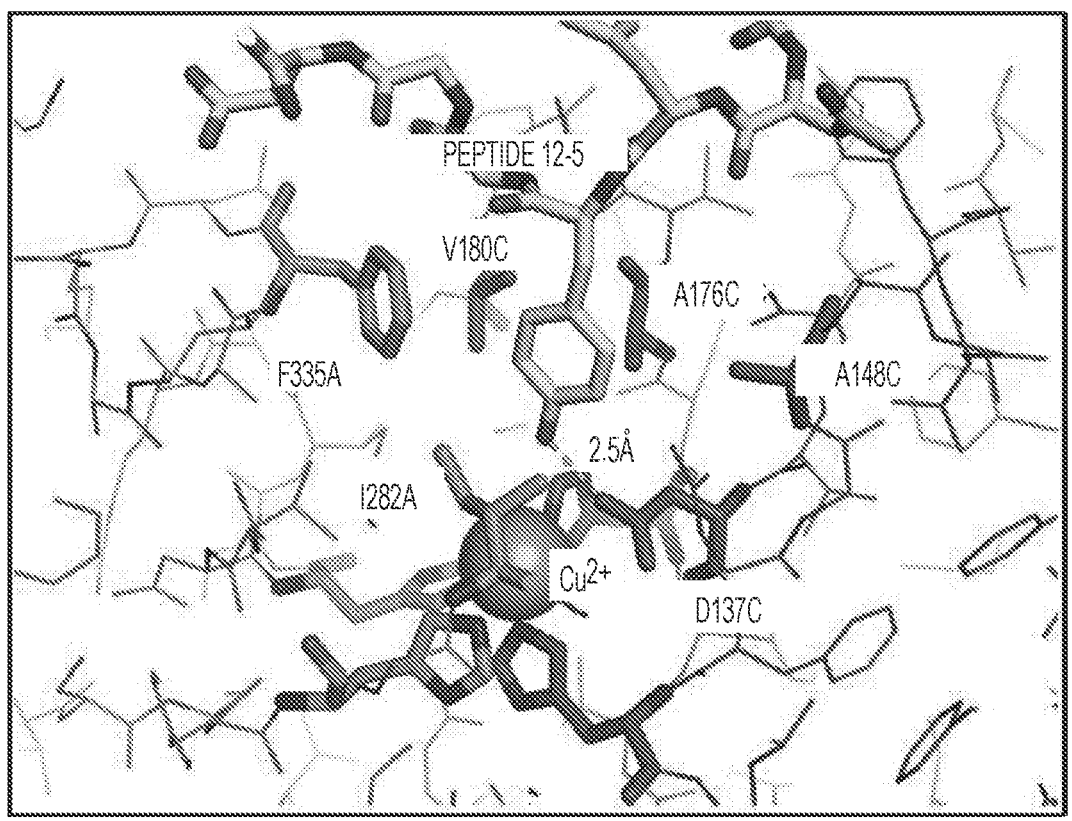
FIG. 5 shows a stick view of the interaction of the peptide 12-5 Tyr side chain in the catalytic active site of AniA homotrimer. The Tyr side chain of the peptide fits in the cavity and established strong van der Waals contact with the hydrophobic residues of the cavity, while the hydroxyl group of the Tyr formed H-bond with the Asp137 residue.
Figure 9:
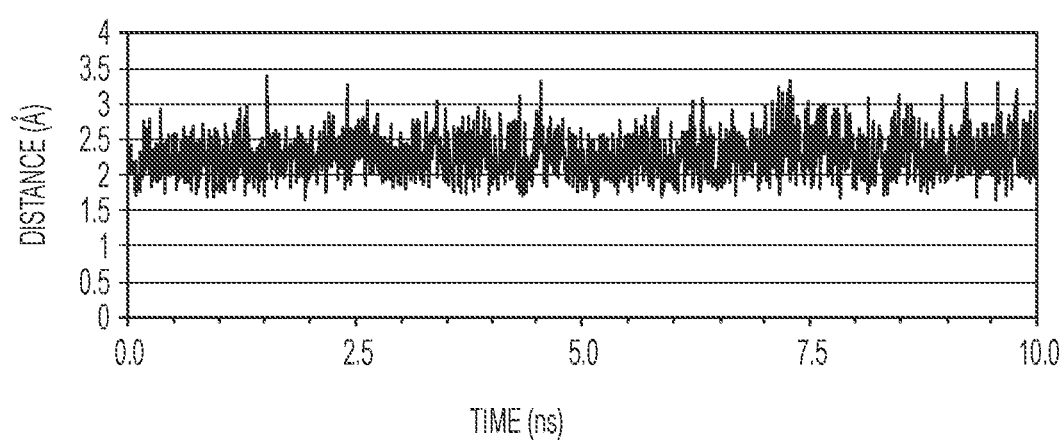
FIG. 9 shows the hydrogen bond (distance) between the hydroxyl group of 12-5 peptide Tyrosine side chain and the carboxylate group of Asp137 residue of AniA homotrimer.

Prediction of the Interactions Between the C7-3 and 12-5 Peptides and AniA. The multi-conformational states of the peptides C7-3 and 12-5 were first generated and the conformations of the peptides with the lowest total energy were positioned on the top of each cavity with an arbitrary distance of ~8 Å. The complexes AniA-peptide were MD simulated in vacuum during 500 ps and the last 20 final snapshots from the trajectory were used to compute the binding free energy. The stabilized peptide conformation with higher binding energy was used for the docking procedure as described in the Materials and Methods. Alternatively, the peptides were docked in the opened $Cu^{2+}$ catalytic active site of the AniA structure. After several docking trials, it was observed that the Tyr side chain of the C7-3 (CNYCRLNLW (SEQ ID NO: 7)) and 12-5 (KHYYGGDTTTLW (SEQ ID NO: 8)) peptides stabilized in the active site by anchoring the Asp137 carboxylate group close to the metal ion ($Cu^{2+}$) while the neighboring residues side chain of the peptide interacted with the active site's residues. The FIG. 5 and FIG. 9 show that the Tyr side chain fit in the cavity and established strong van der Waals contact with the hydrophobic residues of the cavity, while the hydroxyl group of the Tyr formed H-bond with the Asp137 residue. Thereafter, several binding conformations of the peptides were generated and refined using 10 ns MD simulations in explicit water model.

The analysis of the binding energy of the peptides in the different pockets showed that the binding free energy of the peptides C7-3 and 12-5 in the $Cu^{2+}$ catalytic active site was stronger than in the other cavities of the protein complex. The calculated relative free energy was $\Delta\Delta G > -4$ kcal/mol suggesting that the peptides may bind in the other pockets, but the most important binding pose was in the catalytic domain at the interface of the 2 monomers.

Figure 6A:
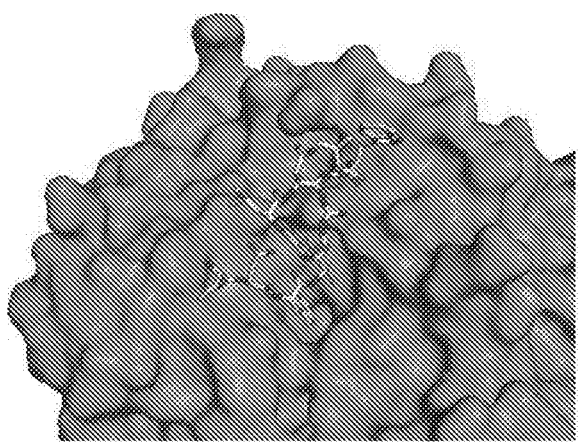
FIGS. 6A-E illustrate binding studies.
Figure 6B:
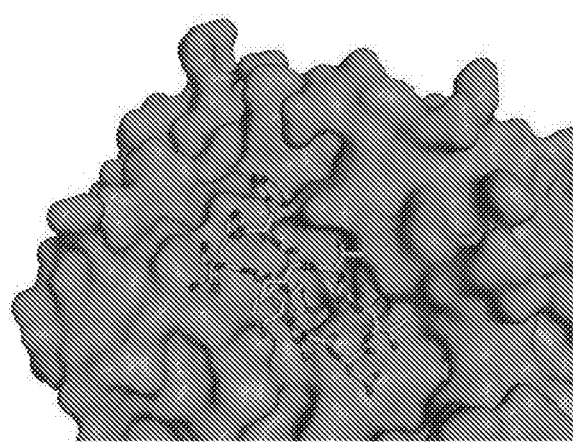
Figure 6C:
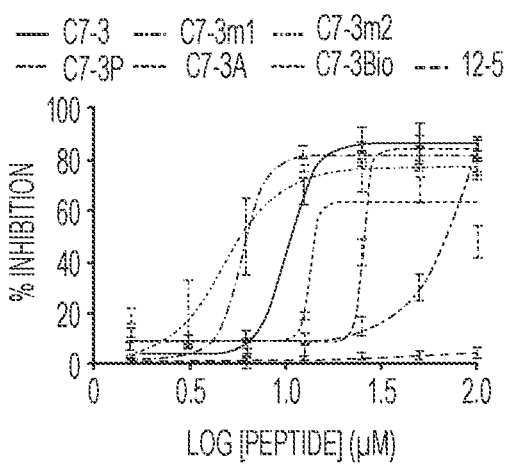
Figure 6D:
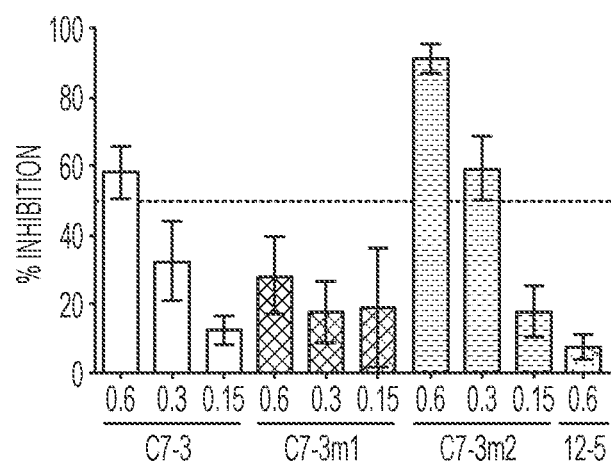
Figure 6E:
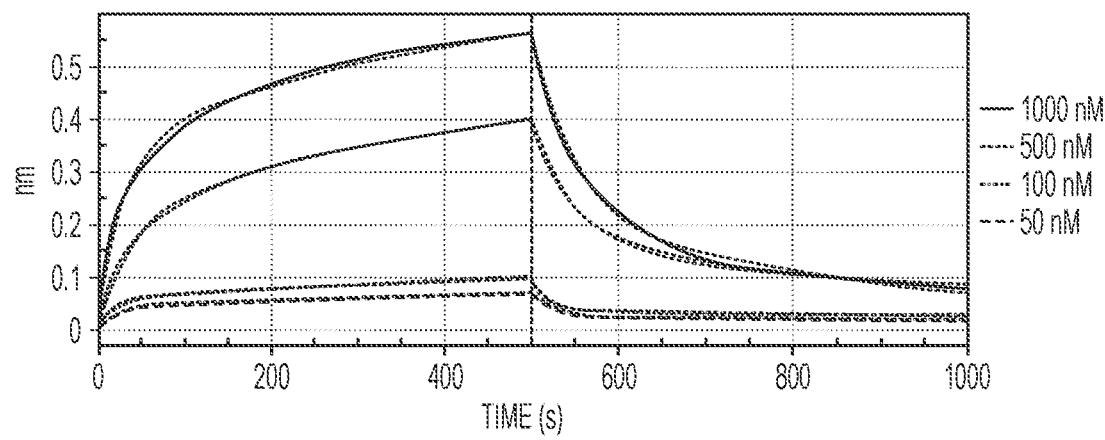

Binding Mode of the C7-3 and 12-5 with AniA Complex. As displayed in FIGS. 6A and B, the two peptides bound in the pocket with distinct conformation. These conformations depended essentially on the residues sequence composing the peptide. Afterward, the initial conformation of the peptide (stable conformation in the solvent) was slightly perturbed during the docking procedure due to the interactions with the receptor.

Finally, based on the docked models it was suggested that the residues near the key Tyr side chain should be: (i) small to prevent steric clashes throughout the docking of the Tyr side chain into the narrow $Cu^{2+}$ pocket and/or (ii) polar so that may establish H-bonds with the residues on the top of the cavity. To validate the peptides binding prediction and highlight the key residues of the peptides involved in the interactions with the receptor some specific residues were mutated in silico and the relative binding free energy of the MD simulated mutants was computed (Table 2).

TABLE 2

In silico analysis of relative binding free energy of the C7-3 and the MD simulated variants interacting in the $Cu^{2+}$ cavity of the AniA homotrimer.

| Peptides | Relative binding free energy (kcal/mol) $\Delta\Delta G = \Delta G(mutant) - \Delta G(wild\ type)$ |
|---|---|
| CNYCRLNLW (SEQ ID NO: 7) | 0.0 (wild type) |
| CNYSRLNLW (SEQ ID NO: 9) | −0.5 |
| CSYCRLNLW (SEQ ID NO: 10) | −0.8 |
| KHYYGGDTTTLW (SEQ ID NO: 8) | 0.0 (wild type) |
| KHYYGNDTTTLW (SEQ ID NO: 11) | −0.6 |
| KHYYGSDTTTLW (SEQ ID NO: 12) | −0.9 |
| KHYYGGDTTSLW (SEQ ID NO: 13) | −0.8 |
| KHYYGGETTTLW (SEQ ID NO: 14) | −0.6 |

Inhibition of AniA Nitrite Reductase Activity by the Heptamer and Dodecamer Peptides. The inhibitory capacity of the two synthesized peptides, C7-3 and 12-5, on the nitrite reductase activity of AniA was assessed in the in vitro nitrite consumption assays with DAN. The efficiency of the inhibition by the peptides was calculated from the rate of nitrite reduction in the presence of various (0 to 100 μM) peptide concentrations. The residual AniA activity (% inhibition) with different peptide concentrations was calculated by comparing the reaction rate of the sAniA alone and with the AniA D137A H280A (FIG. 5 C). These experiments revealed that peptide 12-5 did not influence AniA enzymatic activity (FIG. 5 C), and therefore its additional modifications (Table 2), were not tested. In contrast, C7-3, had a strong inhibitory effect on sAniA with the $IC_{50}$ of 10.15 µM (FIG. 5 C). Next, it was tested whether the Tyr side chain plays a role in the C7-3-AniA interaction by measuring nitrite reductase activity in the presence of increasing concentrations of peptides C7-3A and C7-3P, in which the Tyr residue was replaced with Ala and Phe, respectively. The calculated $IC_{50}$s had estimated values of ~25.18 and >105 µM for C7-3A and C7-3P, demonstrating that replacing Tyr with Phe had detrimental effect on the inhibitor-receptor interaction. Finally, the effect of the replacement of adjacent to Tyr residues (Cys and Asn) with Ser on the inhibitory potential of C7-3 was experimentally verify by including in the nitrite reductase assays peptides C7-3mod1 and C7-3mod2 (Table 2). The $IC_{50}$s decreased about two-fold in comparison to C7-3 and were 5.91 and 4.81 µM for C7-3mod1 and C7-3mod2, respectively (FIG. 5 C).

Inhibition of AniA Nitrite Reductase Activity of Intact *N. gonorrhoeae* Cells. To test whether the C7-3 peptide and its modifications C7-3mod1 and C7-3mod2, as well as 12-5 peptide were capable of blocking AniA enzymatic activity of intact gonococci, *N. gonorrhoeae* FA1090 ΔaniA/$P_{lac}$aniA and ΔaniA/$P_{lac}$aniA D137A H280A were utilized in nitrite consumption assays as described in Materials and Methods. Incubation of ΔaniA/$P_{lac}$aniA cells even with the highest tested concentration of 12-5 peptide (0.6 mM) had no effect on AniA activity, whereas the same concentration of C7-3mod2 gave 90% inhibition (FIG. 6 D). Also, 50% inhibition of nitrite reductase activity was observed with C7-3 and C7-3mod2 at concentrations of 0.6 and 0.3 mM, respectively, and C7-3mod1 inhibited AniA moderately.

Kinetic Analyses of the Interaction Between AniA and C7-3. Subsequently, Bio-Layer Interferometry (BLI) was utilized to study inhibitory interaction between C7-3 and *N. gonorrhoeae* AniA. BLI is a label-free biophysical analysis of small molecule binding and enables the validation and understanding of primary screening actives that provides kinetic data similar to Surface Plasmon Resonance (Concepcion et al. 2009, Comb Chem High Throughput Screen 12:791-800; Shah and Duncan 2014, J Vis Exp doi:10.3791/51383:e51383). Biotinylated C7-3 peptide, C7-3Bio (BiotinAhx-ACNYCRLNLWGGGS-NH$_2$ (SEQ ID NO: 2)), was used with 6-aminohexanoic acid used as a spacer that allowed binding of the peptide to the BLI sensor. First, it was verified that the C7-3Bio peptide was active against AniA by assessing the AniA nitrite reductase activity in the presence of increasing concentrations of the peptide. These experiments gave the $IC_{50}$ of 13.47 µM, a value very close to the $IC_{50}$ of unmodified C7-3 peptide inhibitor (FIG. 6 C). The biotinylated C7-3 was immobilized on disposable streptavidin sensors and incubated with increasing concentrations of AniA. The BLI experiments were performed using steady state method and curve fitting of the association and dissociation responses. Curves were biphasic, indicating that more than one interaction was occurring and the 2:1 heterogenous ligand model gave the calculated $K_D$ value of 775±88.5 nM, confirming strong ligand-receptor interaction.

Altogether, these studies confirmed C7-3 peptide as the first identified inhibitor of nitrite reductase with promising inhibitory activity in vitro as well as in whole cell assay.

DISCUSSION

The antibiotic resistance in *N. gonorrhoeae* continuously challenges treatment regimens and remains public health concern globally (Unemo and 2014, Clin Microbiol Rev 27:587-613; World Health Organization. 2012. Global action plan to control the spread and impact of antimicrobial resistance in *Neisseria gonorrhoeae*. 32 p.; Centers for Disease Control and Prevention. 2013. Antibiotic resistance threats in the United States, 2013. Centers for Disease Control and Prevention, US Department of Health and Human Services). The development of antibacterial compounds with new modes of action, including targeting nonconventional molecules, is critical in battle with this superbug. AniA appears as a suitable non-conventional drug target for several reasons: 1) it is a surface-exposed lipoprotein (Shewell et al. 2013, Biochem Biophys Res Commun 431: 215-20), which warrants accessibility by a potential inhibitor(s); 2) plays pivotal function in the *N. gonorrhoeae* biology; specifically, in denitrification pathway [FIG. 1 D, (Barth et al. 2009, Microbiology 155:4093-103)] and in biofilm formation (Falsetta et al. 2011, Front Microbiol 2:75), and thus its inhibition could affect slowly growing bacteria, which often hamper antimicrobial therapy (Greulich et al. 2015, Mol Syst Biol 11:796); 3) displays high conservation (FIG. 8, (Boulanger and Murphy 2002, J Mol Biol 315:1111-27)] and expression by a wide range of contemporary gonococci as well as during various growth conditions relevant to infection [FIG. 2, (Zielke et al. 2016, Mol Cell Proteomics doi:10.1074/mcp.M116.058800; Zielke et al. 2014, Mol Cell Proteomics 13:1299-317.)]; and 4) crystal structures of AniA, particularly the newly solved l4$_1$22 crystals [FIG. 1, Table 1 and PDB 5UE6, (Boulanger and Murphy 2002, J Mol Biol 315:1111-27)], should be amenable for co-crystallization or soaking experiments with potential inhibitors or small molecule fragments facilitating drug discovery program.

In this study, a phage display approach was applied to identify peptide ligands interacting with AniA (FIG. 3). Phage display technology is a biomolecular tool with applications in basic research and in drug discovery. Ligands identified from screening phage-displayed peptide libraries enabled selection of peptides with affinity to biologically relevant sites on the surface of the target protein (Molek et al. 2011, Molecules 16:857-87; Huang et al. 2012, Antimicrob Agents Chemother 56:4569-82; Pande et al. 2010, Biotechnol Adv 28:849-58). AniA belongs to the surface-exposed copper nitrite reductases, which are responsible for the reduction of nitrite to nitric oxide under oxygen limiting conditions and are primarily found in Gram-negative bacteria (Boulanger and Murphy 2002, J Mol Biol 315:1111-27). AniA forms homotrimers via extensive monomer-monomer interactions [FIG. 1 B-C, (Boulanger and Murphy 2002, J Mol Biol 315:1111-27)]. It was reasoned that a peptide-ligand(s) could interfere with AniA function either directly by binding to the active site cavity or indirectly by either preventing AniA oligomerization or by disrupting the protein-protein interaction with the neisserial azurin Laz protein, which serves as the electron donor for AniA (Woods et al. 1989, Mol Microbiol 3:583-91) or with AccA, a periplasmic copper chaperone that delivers Cu to AniA generating an active nitrite reductase (Jen et al. 2015, FASEB J 29:3828-38). Biopanning experiments with two diverse M13 phage-displayed libraries resulted in discovery of 29 unique peptides (FIG. 3 B). No peptide homologs were found in the databases but searches using two databases, PepBank and SAROTUP (Shtatland et al. 2007, BMC Bioinformatics 8:280; Huang et al. 2010, J Biomed Biotechnol 2010:101932), revealed that none of the identified peptides qualified as target-unrelated. The phage-displayed peptides showed different relative binding affinities in the ELISA that did not correspond to the frequency of phage recovery (FIG. 3B-C). For instance, highly predominant C7-3 peptide which was identified 19 times, showed about two-fold lower relative binding to sAniA in comparison to only once identified 12-5 peptide. This phenomenon has been also observed in other phage display approaches e.g. against the essential cell division protein FtsA (Paradis-Bleau et al. 2008, BMC Biochem 9:33). This could be due to multiple reasons including the phage infection and replication efficiency, folding bias, protein translocation as well as differences in the conformation of the target during direct coating a plastic surface for ELISA versus solution-phase panning with affinity bead capture used in biopanning experiments.

The segments displayed in the Ph.D.-C7C library are flanked by a pair of Cys residues, which are oxidized during phage assembly to a disulfide linkage, resulting in the displayed peptides presented to the target as loops. It was noted, however, that C7-3 contained mutation at the C-terminus of the peptide where instead of the second Cys residue was Trp (FIG. 3B), which affected the way how the peptide was presented to the receptor. Phage-displayed peptide with this mutation must have been enclosed in the original Ph.D.-C7C library. Docking studies of two selected for further evaluation peptides, heptameric C7-3 and dodecameric 12-5, showed several possible interactions with AniA homotrimer (FIGS. 4-5 and 6A-B). Experimental evaluation of these two peptides in biochemical nitrite reductase inhibition as well as whole cell nitrite consumption assays confirmed C7-3 as the promising inhibitor of the AniA nitrite reductase activity (FIG. 6 C-D). Finally, the AniA-C7-3 interaction was also confirmed by BLI experiments with calculated $K_D$ in nanomolar range (FIG. 6 E). It was speculated that 12-5 peptide could bind to the sites of AniA that were not critical for AniA nitrite reductase function or were not accessible in the whole cell assay for instance at the AniA-Laz or AniA-AccA interaction sites.

We initiated optimization of C7-3, by experimental verification of the in-silico alterations of residues adjacent to the key Tyr side chain (Table 2). Of two synthesized derivatives, C7-3mod2, showed both promising $IC_{50}$ in biochemical assay and 90% inhibition of AniA nitrite reductase activity in intact gonococci (FIGS. 6 C and D), supporting that a small and hydrophobic residue adjacent to the key Tyr side chain might enhance the interactions of the peptide ligand with the receptor.

Together, these studies identified the first and potent inhibitor of pivotal gonococcal surface-exposed protein, AniA. Several lines of evidence presented here suggested that C7-3 inhibits AniA by binding into the catalytic active site and characterizing the exact mechanism of this interaction as well as further medicinal chemistry approaches will require co-crystallization of sAniA with the C7-3. In addition, as the C7-3 peptide is directed to the key functional site of AniA, it could be potentially exploited as surrogate ligand in the high-throughput screening campaign of diverse small molecule libraries to identify AniA inhibitors.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. An isolated peptide, comprising the amino acid sequence set forth as $CX_1YX_2RLNLW$ (SEQ ID NO: 37), wherein $X_1$ can be a N or S, and wherein $X_2$ can be a N or S.

2. A composition comprising one or more peptides of claim 1, and a pharmaceutically acceptable carrier.

3. The composition of claim 2, further comprising an antibiotic agent.

4. An isolated peptide comprising the amino acid sequence set forth as one of SEQ ID NO: 7, SEQ ID NO: 9, and SEQ ID NO: 10.

5. The isolated peptide of claim 4, wherein the amino acid sequence further comprises the amino acid sequence GGGS (SEQ ID NO: 38) on the C-terminal end.

6. The isolated peptide of claim 5, wherein the amino acid sequence is set forth as one of SEQ ID NO: 2, SEQ ID NO: 3, and SEQ ID NO: 4.

7. A composition comprising one or more peptides of claim 4, and a pharmaceutically acceptable carrier.

8. The composition of claim 7, further comprising an antibiotic agent.

9. A method of treating and/or inhibiting *Neisseria gonorrhoeae* infection in a subject, comprising:
   selecting a subject for treatment that has, or is at a risk for developing, an infection by *Neisseria gonorrhoeae*; and
   administering to a subject a therapeutically effective amount of the composition of claim 7, thereby treating and/or inhibiting *Neisseria gonorrhoeae* infection in the subject.

10. The method of claim 9, wherein the amino acid sequence further comprises the amino acid sequence GGGS (SEQ ID NO: 38) on the C-terminal end.

11. The method of claim 10, wherein the amino acid sequence is set forth as one of SEQ ID NO: 2, SEQ ID NO: 3, and SEQ ID NO: 4.

12. A method of inhibiting AniA enzymatic activity in a cell comprising:

contacting a cell expressing AniA with an effective amount of the peptide of claim 4, thereby inhibiting AniA enzymatic activity in the cell.

13. The method of claim 12, wherein the amino acid sequence further comprises the amino acid sequence GGGS (SEQ ID NO: 38) on the C-terminal end.

14. The method of claim 13, wherein the amino acid sequence is the amino acid sequences set forth as one of SEQ ID NO: 2, SEQ ID NO: 3, and SEQ ID NO: 4.

15. The method of claim 12, further comprising, contacting the cell with an effective amount of an antibiotic for *Neisseria gonorrhoeae*.

16. The method of claim 12, wherein the cell is a *Neisseria gonorrhoeae* cell.

17. A method of treating and/or inhibiting *Neisseria gonorrhoeae* infection in a subject, comprising:

selecting a subject for treatment that has, or is at a risk for developing, an infection by *Neisseria gonorrhoeae*; and administering to a subject a therapeutically effective amount of the composition of claim 2, thereby treating and/or inhibiting *Neisseria gonorrhoeae* infection in the subject.

18. A method of inhibiting AniA enzymatic activity in a cell, comprising:

contacting a cell expressing AniA with an effective amount of the peptide of claim 1, thereby inhibiting AniA enzymatic activity in the cell.

19. The method of claim 18, wherein the amino acid sequence further comprises the amino acid sequence GGGS (SEQ ID NO: 38) on the C-terminal end.

20. The method of claim 19, further comprising, contacting the cell with an effective amount of an antibiotic for *Neisseria gonorrhoeae* .

* * * * *